US012773142B2

(12) United States Patent
Haga

(10) Patent No.: US 12,773,142 B2
(45) Date of Patent: Oct. 27, 2026

(54) DETECTION DEVICE

(71) Applicant: Japan Display Inc., Tokyo (JP)

(72) Inventor: Yuta Haga, Tokyo (JP)

(73) Assignee: Japan Display Inc., Tokyo (JP)

( * ) Notice: Subject to any disclaimer, the term of this patent is extended or adjusted under 35 U.S.C. 154(b) by 390 days.

(21) Appl. No.: 18/513,154

(22) Filed: Nov. 17, 2023

(65) Prior Publication Data

US 2024/0172972 A1 May 30, 2024

(30) Foreign Application Priority Data

Nov. 25, 2022 (JP) ................................ 2022-188184

(51) Int. Cl.
*A61B 5/1455* (2006.01)

(52) U.S. Cl.
CPC ................................ *A61B 5/14552* (2013.01)

(58) Field of Classification Search
CPC ............ A61B 5/02427; A61B 5/02433; A61B 5/7203; A61B 5/7214; A61B 5/7221; A61B 5/7235; A61B 5/72; A61B 2562/00; A61B 2562/043; A61B 2562/046; A61B 2562/04; A61B 2562/06; A61B 2562/063; A61B 2562/066; A61B 5/14542; A61B 5/1455; A61B 5/14551; A61B 5/14552; A61B 5/6826
USPC .......................................................... 600/323
See application file for complete search history.

(56) References Cited

U.S. PATENT DOCUMENTS

| | | | | | |
|---|---|---|---|---|---|
| 4,714,080 | A * | 12/1987 | Edgar, Jr. | A61B 5/14551 | 600/479 |
| 2009/0326347 | A1* | 12/2009 | Scharf | A61B 5/14552 | 600/323 |
| 2013/0261415 | A1* | 10/2013 | Ashe | A61B 5/14552 | 600/323 |

(Continued)

FOREIGN PATENT DOCUMENTS

| | | | | |
|---|---|---|---|---|
| CN | 201104882 | Y * | 8/2008 | |
| EP | 0957747 | B1 * | 2/2004 | A61B 5/14552 |

(Continued)

OTHER PUBLICATIONS

Office Action issued in corresponding Japanese patent application No. 2022-188184, mailed on Jan. 20, 2026 and English translation of same. 6 pages.

*Primary Examiner* — Brian L Casler
(74) *Attorney, Agent, or Firm* — K&L Gates LLP

(57) ABSTRACT

According to an aspect, a detection device includes: a first optical sensor configured to detect light; a second optical sensor provided adjacent to the first optical sensor and configured to detect light; a first light source configured to emit light having a predetermined wavelength; a second light source configured to emit light having a wavelength different from that of the light emitted by the first light source; a controller configured to cause the first light source and the second light source to simultaneously emit the light; and a signal processor configured to perform processing to obtain a blood oxygen saturation level based on a value detected by the first optical sensor and a value detected by the second optical sensor. The first optical sensor and the second optical sensor are configured to detect light that has been reflected in a living body or transmitted through the living body.

12 Claims, 22 Drawing Sheets

(56) References Cited

U.S. PATENT DOCUMENTS

| | | | | |
|---|---|---|---|---|
| 2015/0230743 | A1* | 8/2015 | Silveira ................ | A61B 5/7282<br>600/323 |
| 2016/0358332 | A1 | 12/2016 | Watanabe | |
| 2021/0326623 | A1* | 10/2021 | Kato ....................... | H10F 55/00 |

FOREIGN PATENT DOCUMENTS

| | | | | | |
|---|---|---|---|---|---|
| JP | 2013-000158 | A | | 1/2013 | |
| JP | 5544158 | B2 | | 7/2014 | |
| JP | 2019513035 | A | * | 5/2019 | ......... A61B 5/02416 |
| JP | 2019180861 | A | | 10/2019 | |
| JP | 2021-045600 | A | | 3/2021 | |

* cited by examiner

| | PIXEL (A) | PIXEL (B) |
|---|---|---|
| $SpO2_1$ | Pix1 | Pix3 |
| $SpO2_2$ | Pix1 | Pix4 |
| $SpO2_3$ | Pix2 | Pix3 |
| $SpO2_4$ | Pix2 | Pix4 |

DETECTION DEVICE

CROSS-REFERENCE TO RELATED APPLICATION

This application claims the benefit of priority from Japanese Patent Application No. 2022-188184 filed on Nov. 25, 2022, the entire contents of which are incorporated herein by reference.

BACKGROUND

1. Technical Field

What is disclosed herein relates to a detection device.

2. Description of the Related Art

Detection devices are known that emit light into a body through the skin thereof and acquire an oxygen saturation level in blood (hereinafter, called "blood oxygen saturation level SpO2") based on transcutaneous data acquired by detecting light transmitted through or reflected by arteries. The blood oxygen saturation level SpO2 refers to a ratio of an amount of oxygen actually bound to hemoglobin to the total amount of oxygen under the assumption that the oxygen is bound to all the hemoglobin in the blood. In a case of acquiring the blood oxygen saturation level SpO2, for example, a pulse wave acquired by infrared light and a pulse wave acquired by red light are used (refer to Japanese Patent Application Laid-open Publication No. 2019-180861, for example).

As described above, to acquire the blood oxygen saturation level $SpO_2$, the pulse waves need to be acquired by the light having two different wavelengths. In the case of acquiring the pulse waves by the light having two different wavelengths, data can be considered to be acquired at different timings in a time-division manner, for example. That is, a time-divisional process can be considered in which pulse wave data is acquired by the first wavelength light, and then, pulse wave data is acquired by the second wavelength light. However, when considering efficiently acquiring the blood oxygen saturation level, the time-divisional process described above has its limitations.

For the foregoing reasons, there is a need for a detection device capable of efficiently acquiring the blood oxygen saturation level.

SUMMARY

According to an aspect, a detection device includes: a first optical sensor configured to detect light; a second optical sensor provided adjacent to the first optical sensor and configured to detect light; a first light source configured to emit light having a predetermined wavelength; a second light source configured to emit light having a wavelength different from that of the light emitted by the first light source; a controller configured to cause the first light source and the second light source to simultaneously emit the light; and a signal processor configured to perform processing to obtain a blood oxygen saturation level based on a value detected by the first optical sensor and a value detected by the second optical sensor. The first optical sensor and the second optical sensor are configured to detect light that has been reflected in a living body or transmitted through the living body.

DETAILED DESCRIPTION

Figure 1:
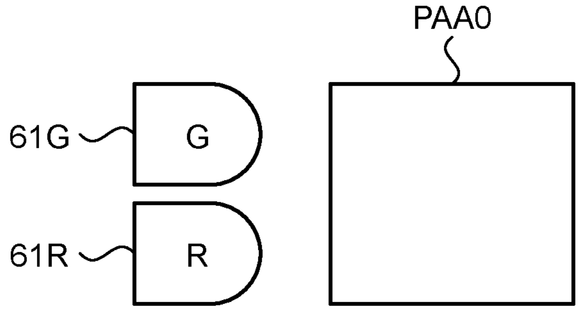
FIG. 1 is a diagram illustrating main component parts of a detection device according to a comparative example.

The following describes a mode (embodiment) for carrying out the present invention in detail with reference to the drawings. The present disclosure is not limited to the description of the embodiment given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the present disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the present disclosure and the drawings, and detailed description thereof may not be repeated where appropriate.

In the present specification and claims, in expressing an aspect of disposing another structure on or above a certain structure, a case of simply expressing "on" includes both a case of disposing the other structure immediately on the certain structure so as to contact the certain structure and a case of disposing the other structure above the certain structure with still another structure interposed therebetween, unless otherwise specified.

Comparative Example

To facilitate understanding of the present disclosure, a comparative example will first be described. FIG. 1 is a diagram illustrating main component parts of a detection device according to the comparative example. As illustrated in FIG. 1, the detection device according to the comparison example includes a red light source 61R, a green light source 61G, and an optical sensor PAA0. "R" in the figure indicates a light source for red light, and "G" in the figure indicates a light source for green light. The same also applies to the other figures.

The green light source 61G emits green light. The green light has a wavelength of 490 nm to 550 nm, for example. The red light source 61R emits red light. The red light has a wavelength of 640 nm to 770 nm, for example. That is, the green light source 61G and the red light source 61R emit light having wavelengths different from each other. The optical sensor PAA0 detects light. The optical sensor PAA0 is provided in common to the red light source 61R and the green light source 61G. The optical sensor PAA0 can detect the red light and the green light.

Figure 2:
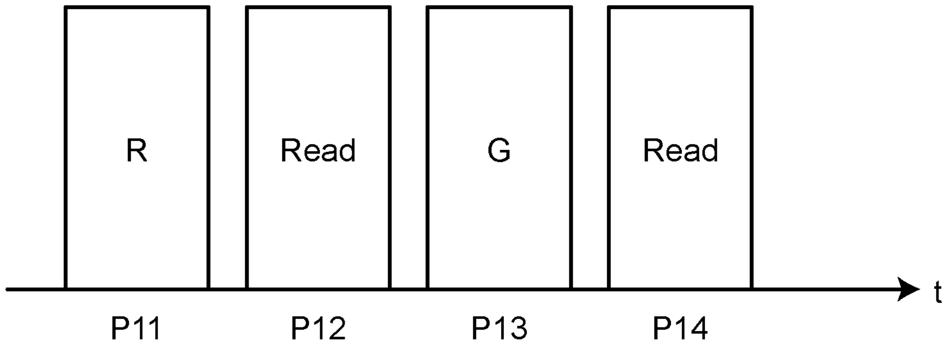
FIG. 2 is a diagram illustrating an operation example of the detection device illustrated in FIG. 1.

In the comparative example illustrated in FIG. 1, the red and the green light sources 61R and 61G are alternately turned on, and the light thereof is received by the optical sensor PAA0. FIG. 2 is a diagram illustrating an operation example of the detection device illustrated in FIG. 1. In FIG. 2, the horizontal axis indicates passage of time and the vertical axis indicates a specific operation. As illustrated in FIG. 2, in this example, the red light source 61R is first turned on to emit red light, and the optical sensor PAA0 detects the red light (Period P11). Then, the data detected by the optical sensor PAA0 is read (Period P12). Subsequently, the green light source 61G is turned on to emit green light, and the optical sensor PAA0 detects the green light (Period P13). Then, the data detected by the optical sensor PAA0 is read (Period P14). Thus, in the comparative example illustrated in FIGS. 1 and 2, the red and the green light sources 61R and 61G that emit the light having wavelengths different from each other are alternately turned on, and the pieces of data corresponding to the light sources are acquired in a time-division manner.

Main Configuration of Detection Device

Figure 3:
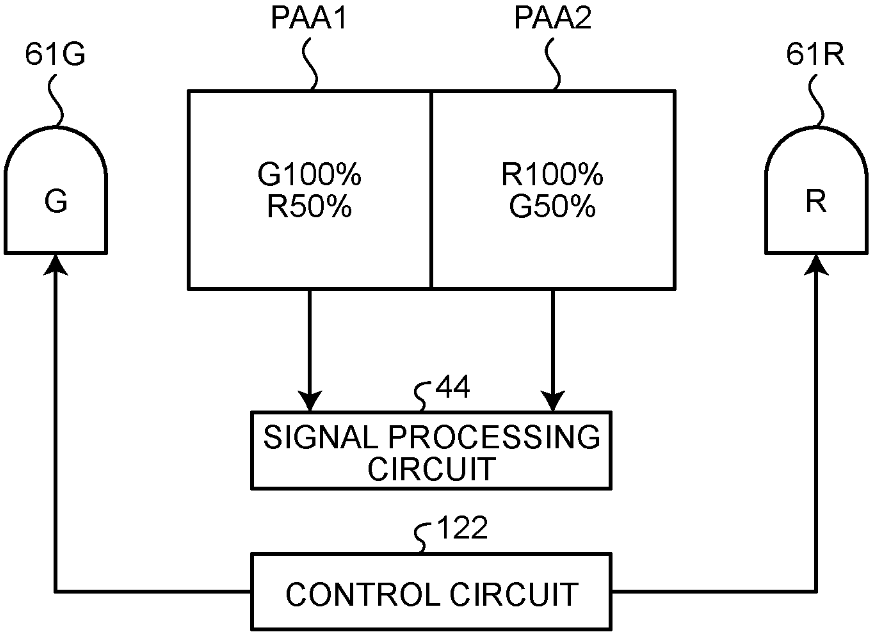
FIG. 3 is a diagram illustrating a main configuration of a detection device according to the present disclosure.

FIG. 3 is a diagram illustrating a main configuration of a detection device according to the present disclosure. As illustrated in FIG. 3, the detection device of the present disclosure includes the red light source 61R, the green light source 61G, an optical sensor PAA1, an optical sensor PAA2, a control circuit 122, and a signal processing circuit 44. The signal processing circuit 44 corresponds to a signal processor of the present disclosure.

The green light source 61G serving as a first light source emits green light. The red light source 61R serving as a second light source emits red light. That is, the green light source 61G and the red light source 61R emit light having wavelengths different from each other.

The control circuit 122 functions as a controller that causes the red light source 61R and the green light source 61G to emit light. The control circuit 122 causes the green and the red light sources 61G and 61R to simultaneously emit light.

The optical sensor PAA1 serving as a first optical sensor detects light. The optical sensor PAA2 serving as a second optical sensor is provided adjacent to the optical sensor PAA1. The optical sensor PAA1 serving as the first optical sensor is provided at a location interposed between the optical sensor PAA2 serving as the second optical sensor and the green light source 61G serving as the first light source. The optical sensor PAA2 serving as the second optical sensor is provided at a location interposed between the optical sensor PAA1 serving as the first optical sensor and the red light source 61R serving as the second light source.

The signal processing circuit 44 performs processing to obtain a blood oxygen saturation level based on a value detected by the optical sensor PAA1 and a value detected by the optical sensor PAA2.

In the detection device illustrated in FIG. 3, green light emitted from the green light source 61G enters a living body, which is not illustrated. Red light emitted from the red light source 61R enters the living body, which is not illustrated. The optical sensors PAA1 and PAA2 detect light transmitted through the living body (not illustrated) or reflected at the living body (not illustrated).

Figure 4:
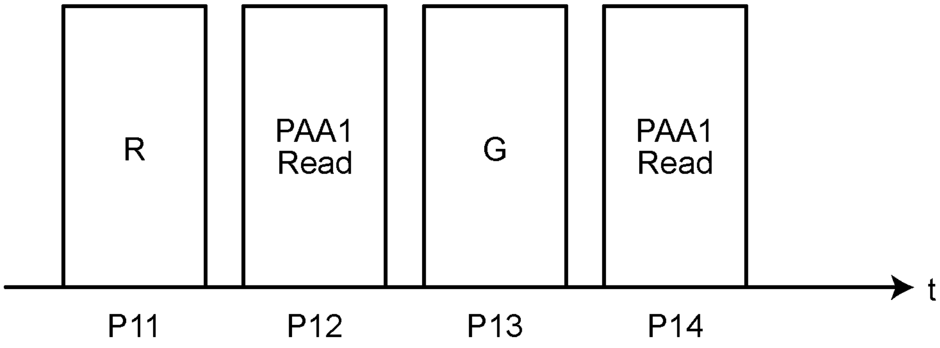
FIG. 4 is a diagram illustrating an operation example of the detection device illustrated in FIG. 3.

Consider a case where the detection device illustrated in FIG. 3 is operated in the same way as in FIG. 2. FIG. 4 is a diagram illustrating an operation example of the detection device illustrated in FIG. 3. In FIG. 4, the horizontal axis indicates passage of time and the vertical axis indicates a specific operation. As illustrated in FIG. 4, when the red and the green light sources 61R and 61G are alternately turned on, the red light source 61R is first turned on to emit red light, and the optical sensor PAA1 detects the red light (Period P11). Then, the data detected by the optical sensor PAA1 is read (Period P12). Subsequently, the green light source 61G is turned on to emit green light, and the optical sensor PAA1 detects the green light (Period P13). Then, the data detected by the optical sensor PAA1 is read (Period P14). Thus, when the red and the green light sources 61R and 61G that emit light having wavelengths different from each other are alternately turned on, the pieces of data corresponding to the respective light sources are acquired in a time-division manner.

Figure 5:
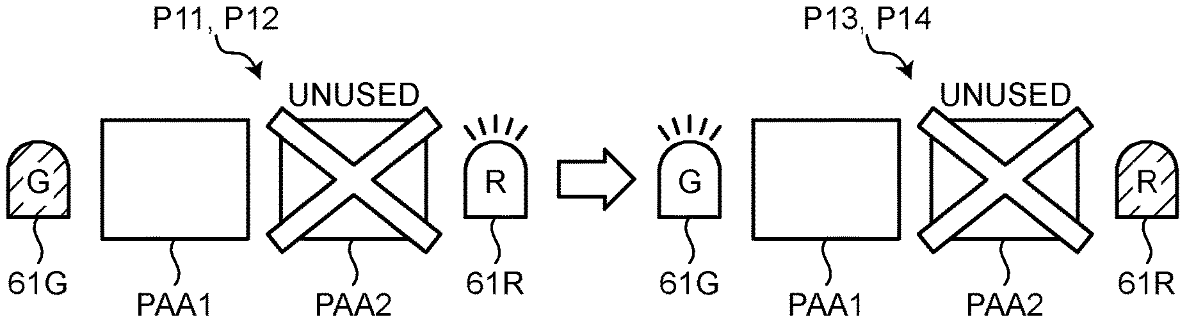
FIG. 5 is a diagram illustrating a state of use of optical sensors in the case of the operation example illustrated in FIG. 4.

FIG. 5 is a diagram illustrating a state of use of the optical sensors PAA1 and PAA2 in the case of the operation example illustrated in FIG. 4. As illustrated in FIG. 5, during Periods P11 and P12, the red light source 61R is caused to be on and the green light source 61G is caused to be off. The optical sensor PAA1 detects the red light, and the data detected by the optical sensor PAA1 is read. During Periods P13 and P14, the green light source 61G is caused to be on, and the red light source 61R is caused to be off. The optical sensor PAA1 detects the green light, and the data detected by the optical sensor PAA1 is read. Thus, when the red and the green light sources 61R and 61G are alternately turned on, the optical sensor PAA1 is used and the optical sensor PAA2 is not used from Period P11 to Period P14.

Figure 6:
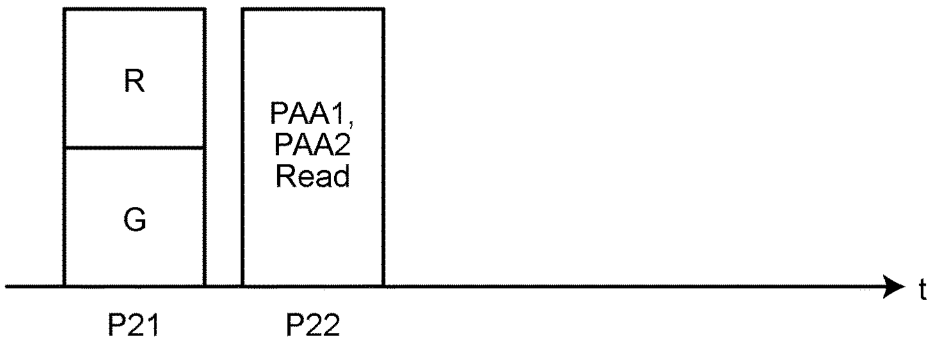
FIG. 6 is a diagram illustrating an operation example of the detection device of the present disclosure.

In contrast to the operation example described with reference to FIG. 4, the detection device of the present disclosure is operated as described below. FIG. 6 is a diagram illustrating an operation example of the detection device of the present disclosure. In FIG. 6, the horizontal axis indicates passage of time and the vertical axis indicates a specific operation. As illustrated in FIG. 6, in this example, the red and the green light sources 61R and 61G are simultaneously turned on (Period P21). That is, the red and the green light sources 61R and 61G that emit light having wavelengths different from each other are simultaneously turned on. Then, the data detected by the optical sensors PAA1 and PAA2 are read (Period P22). Thus, the red and the green light sources 61R and 61G that emit light having wavelengths different from each other are simultaneously turned on, and the pieces of data corresponding to the light sources are acquired from the optical sensors PAA1 and PAA2.

Figure 7:
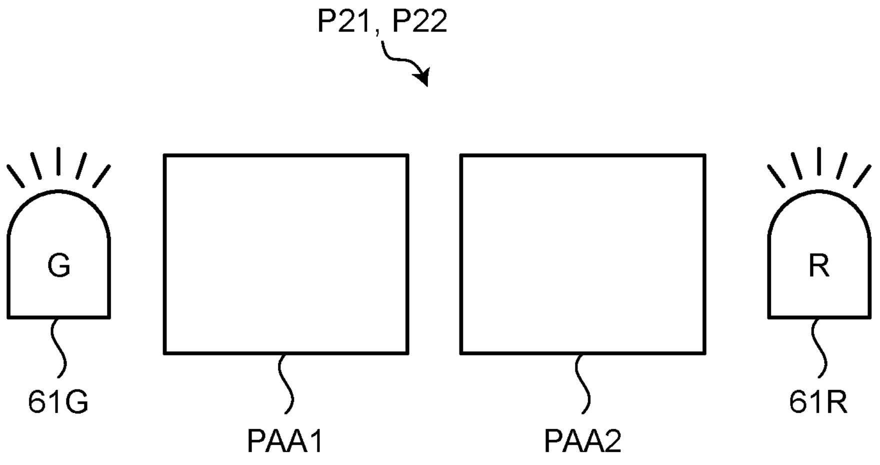
FIG. 7 is a diagram illustrating a state of use of the optical sensors in the case of the operation example illustrated in FIG. 6.

FIG. 7 is a diagram illustrating a state of use of the optical sensors PAA1 and PAA2 in the case of the operation example illustrated in FIG. 6. As illustrated in FIG. 7, the red and the green light sources 61R and 61G are simultaneously turned on during Period P21. The optical sensor PAA1 detects light including the red light and the green light, and the data detected by the optical sensor PAA1 is read. At the same time, the optical sensor PAA2 detects the light including the red light and the green light, and the data detected by the optical sensor PAA2 is read. That is, from Period P21 to Period P22, the optical sensors PAA1 and PAA2 are used to acquire the pieces of data corresponding to the light sources.

Referring back to FIG. 3, the following describes the optical sensor PAA1. The optical sensor PAA1 is located at a shorter distance from the green light source 61G than from the red light source 61R. The distance from the optical sensor PAA1 to the green light source 61G is shorter than the distance from the optical sensor PAA1 to the red light source 61R. Therefore, if, of the light detected by the optical sensor PAA1, the green light (G) is assumed to be, for example, 100%, the red light (R) is detected to be, for example, 50%. That is, in the optical sensor PAA1, the detected value of the red light is approximately half the detected value of the green light.

The following describes the optical sensor PAA2. The optical sensor PAA2 is located at a shorter distance from the red light source 61R than from the green light source 61G. The distance from the optical sensor PAA2 to the red light source 61R is shorter than the distance from the optical sensor PAA2 to the green light source 61G. Therefore, if, of the light detected by the optical sensor PAA2, the red light (R) is assumed to be, for example, 100%, the green light (G) is detected to be, for example, 50%. That is, in the optical sensor PAA2, the detected value of the green light is approximately half the detected value of the red light. As described above, in each of the optical sensors PAA1 and PAA2, the arrival ratio of the red light from the red light source 61R differs from that of the green light from the green light source 61G. The red light is known to reach farther than the green light does. A smaller component of the green light reaches far because of being attenuated by a larger amount in vivo.

As described with reference to FIGS. 2 and 4, when the green and the red light sources 61G and 61R are alternately turned on, and the pieces of data corresponding to the light sources are acquired in a time-division manner, the frame rate cannot be increased. The frame rate is the number of times the data can be acquired in a time corresponding to one frame. In contrast, the frame rate at which data is acquired can be increased by simultaneously turning on the red and the green light sources 61R and 61G, as described with reference to FIG. 6. When the data is acquired by simultaneously turning on the red and the green light sources 61R and 61G, the frame rate is doubled compared with the case of acquiring the pieces of data corresponding to the light sources in a time-division manner. By increasing the frame rate, a blood oxygen saturation level SpO2 can be calculated more efficiently. When the green and the red light sources 61G and 61R are alternately turned on to acquire the pieces of data corresponding to the respective light sources in a time-division manner, the blood oxygen saturation level SpO2 is calculated by Expression (1) using pulse wave data.

$$\mathrm{SpO_2} = b - a \cdot R \tag{1}$$

In Expression (1) given above, “a” and “b” denote predetermined coefficients determined in advance based on actual measurement values. In Expression (1), R is defined by Expression (2) below.

$$R = \frac{\mathrm{AC(Red)/DC(Red)}}{\mathrm{AC}(Gr)/\mathrm{DC}(Gr)} \tag{2}$$

In Expression (2) given above, AC (Red) denotes an alternating-current (AC) component of a measurement value of the red light; DC (Red) denotes a direct-current (DC) component of the measurement value of the red light; AC (Gr) denotes the AC component of a measurement value of the green light; and DC (Gr) denotes the DC component of the measurement value of the green light. The AC component includes a pulse wave component.

The optical sensors may be planarly arranged in vertical and horizontal directions to form a detection area for detecting light. Two pixels included in such a detection area may be the two optical sensors PAA1 and PAA2 described above. That is, each pixel serves as an optical sensor. When two light sources are simultaneously turned on as illustrated in FIG. 7, and the data of the two pixels is acquired, the following result is obtained. That is, when a pixel Pix1 and a pixel Pix2 are used, the blood oxygen saturation level SpO2 is calculated by Expression (3) using the pulse wave data.

$$SpO_2 = b' - a' \cdot R' \quad (3)$$

In Expression (3) given above, "a'" and "b'" denote predetermined coefficients determined in advance based on actual measurement values. The coefficients "a'" and "b'" are values different from "a" and "b". In Expression (3), R' is defined by the Expression (4) below.

$$R' = \frac{AC(Pix1)/DC(Pix1)}{AC(Pix2)/DC(Pix2)} \quad (4)$$

In Expression (4) given above, AC (Pix1) denotes the AC component of a measurement value of a first pixel; DC (Pix1) denotes the DC component of the measurement value of the first pixel; AC (Pix2) denotes the AC component of a measurement value of a second pixel; and DC (Pix2) denotes the DC component of the measurement value of the second pixel. The AC component includes a pulse wave component.

Figure 8:
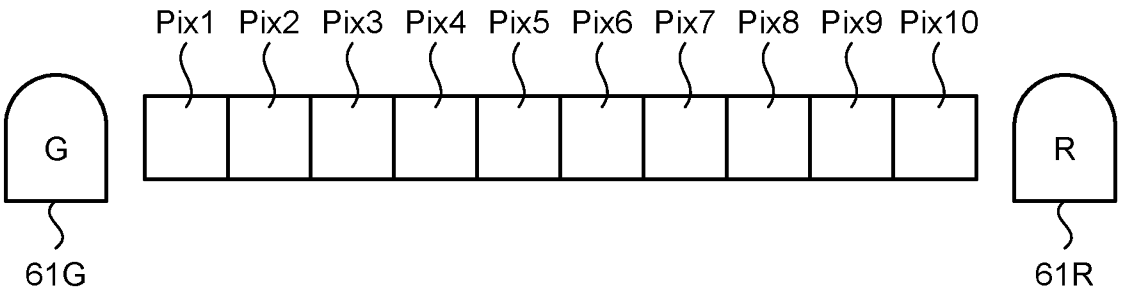
FIG. 8 is a diagram illustrating an example in a case where ten pixels are used in the detection device.

While the above has described the case where the first and the second pixels corresponding to the two optical sensors PAA1 and PAA2 are used, three or more pixels may be used. FIG. 8 is a diagram illustrating an example in a case where ten pixels are used in the detection device. As illustrated in FIG. 8, this example uses pixels Pix1 to Pix10, the green light source 61G, and the red light source 61R. The pixels Pix1 to Pix10 are provided at locations interposed between the green light source 61G and the red light source 61R.

In FIG. 8, the red and the green light sources 61R and 61G are simultaneously turned on. Then, light having different ratios of the green light to the red light is detected by the respective pixels Pix1 to Pix10. Therefore, by focusing on any two of the pixels, SpO2 can be calculated by Expressions (3) and (4) given above. SpO2 may be calculated a plurality of times by sequentially focusing on two of the pixels, and the average of the results of those calculations may be obtained. For example, a first value of SpO2 can be calculated using the pixels Pix1 and Pix9; a second value of SpO2 can be calculated using the pixels Pix1 and Pix10; a third value of SpO2 can be calculated using the pixels Pix2 and Pix9; a fourth value of SpO2 can be calculated using the pixels Pix2 and Pix10; and then, the average value of the four calculation results may be obtained. If each of the pixels contains independent noise components, the noise components can be effectively removed by calculating the averaged value of SpO2.

Figures 9, 10:
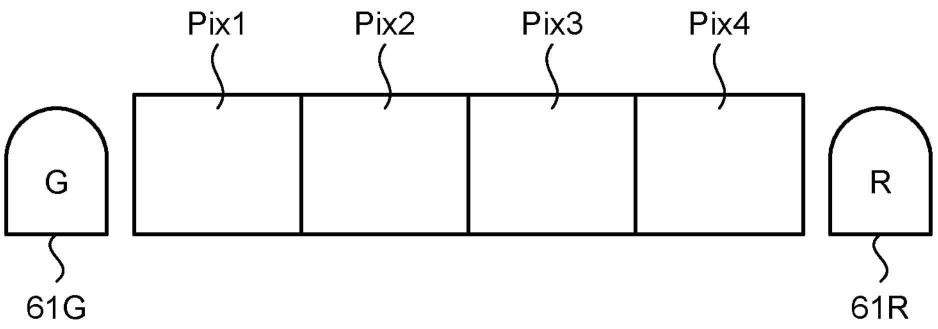
FIG. 9 is a diagram illustrating an example in a case where SpO2 is calculated using four pixels.
FIG. 10 is a diagram illustrating an exemplary combination table in a case where two of the four pixels are combined.

The following describes a more specific calculation of the blood oxygen saturation level SpO2 in the case of using a larger number of pixels. FIG. 9 is a diagram illustrating an example in a case where SpO2 is calculated using four pixels in the detection device. In FIG. 9, the pixel Pix3 serving as a third optical sensor and the pixel Pix4 serving as a fourth optical sensor are used in addition to the pixel Pix1 serving as the first optical sensor and the pixel Pix2 serving as the second optical sensor. That is, four pixels are used in FIG. 9. FIG. 10 is a diagram illustrating an exemplary combination table in a case where two of the four pixels are combined. FIG. 10 illustrates the exemplary combination table in the case of combining a pixel (A) with a pixel (B). This combination table is stored in a storage circuit 46 and referred to by the signal processing circuit 44, as will be described later.

As illustrated in FIG. 9, this example uses the four pixels Pix1, Pix2, Pix3, and Pix4, and the red and the green light sources 61R and 61G. The four pixels Pix1 to Pix4 are provided at locations interposed between the green light source 61G and the red light source 61R.

As illustrated in FIG. 10, the pixels Pix1 and Pix3 are used when calculating the blood oxygen saturation level $SpO2_1$. That is, the data of the pixel Pix1 and the data of the pixel Pix3 are used. Expressions (5) and (6) given below are used to calculate the blood oxygen saturation level $SpO2_1$.

$$SpO_{2_1} = b_1 - a_1 \cdot R_1 \quad (5)$$

$$R_1 = \frac{AC(Pix1)/DC(Pix1)}{AC(Pix3)/DC(Pix3)} \quad (6)$$

As illustrated in FIG. 10, the pixels Pix1 and Pix4 are used when calculating the blood oxygen saturation level $SpO2_2$. That is, the data of the pixel Pix1 and the data of the pixel Pix4 are used. Expressions (7) and (8) given below are used to calculate the blood oxygen saturation level $SpO2_2$.

$$SpO_{2_2} = b_2 - a_2 \cdot R_2 \quad (7)$$

$$R_2 = \frac{AC(Pix1)/DC(Pix1)}{AC(Pix4)/DC(Pix4)} \quad (8)$$

As illustrated in FIG. 10, the pixels Pix2 and Pix3 are used when calculating the blood oxygen saturation level $SpO2_3$. That is, the data of the pixel Pix2 and the data of the pixel Pix3 are used. Expressions (9) and (10) given below are used to calculate the blood oxygen saturation level $SpO2_3$.

$$SpO_{2_3} = b_3 - a_3 \cdot R_3 \quad (9)$$

$$R_3 = \frac{AC(Pix2)/DC(Pix2)}{AC(Pix3)/DC(Pix3)} \quad (10)$$

As illustrated in FIG. 10, the pixels Pix2 and Pix4 are used when calculating the blood oxygen saturation level $SpO2_4$. That is, the data of the pixel Pix2 and the data of pixel Pix4 are used. Expressions (11) and (12) given below are used to calculate the blood oxygen saturation level $SpO2_4$.

$$SpO_{2_4} = b_4 - a_4 \cdot R_4 \quad (11)$$

$$R_4 = \frac{AC(Pix2)/DC(Pix2)}{AC(Pix4)/DC(Pix4)} \quad (12)$$

Finally, the average value of the calculated values of Expressions (5), (7), (9), and (11) above is calculated. That is, Expression (13) given below is used to calculate the average value of the blood oxygen saturation levels SpO2.

$$SpO_2 = \frac{SpO_{2_1} + SpO_{2_2} + SpO_{2_3} + SpO_{2_4}}{4} \quad (13)$$

In Expressions (5), (7), (9), and (11) given above, coefficients $a_1$, $a_2$, $a_3$, and $a_4$ and coefficients $b_1$, $b_2$, $b_3$, and $b_4$ are predetermined coefficients determined in advance based on actual measurement values. The coefficients $a_1$, $a_2$, $a_3$, and $a_4$ and the coefficients $b_1$, $b_2$, $b_3$, and $b_4$ have values different from one another because the mixing ratio between the green light from the green light source 61G and the red light from the red light source 61R varies. That is, different coefficients are used for each combination of the pixels. These coefficients are stored as an SpO2 calculation parameter table in the storage circuit 46 (refer to FIG. 14).

Figure 11:
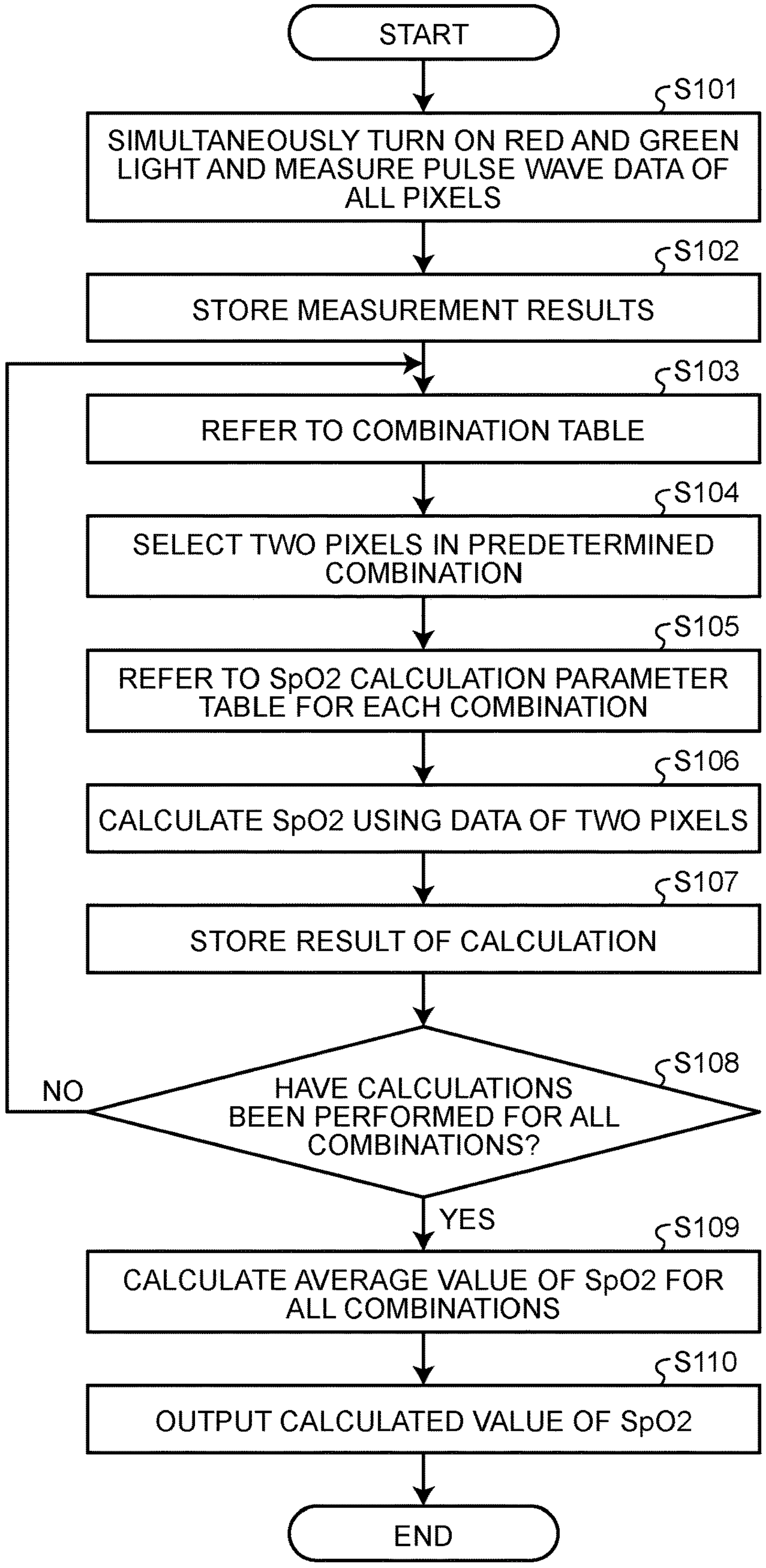
FIG. 11 is a flowchart illustrating a process of calculating the blood oxygen saturation levels SpO2 using the pixels and calculating the average value thereof.

The following describes a process of calculating the blood oxygen saturation levels SpO2 using the multiple pixels and calculating the average value thereof as described above, with reference to FIG. 11. FIG. 11 is a flowchart illustrating the process of calculating the blood oxygen saturation levels SpO2 using the multiple pixels and calculating the average value thereof. This process is mainly performed in the signal processing circuit 44.

In FIG. 11, the control circuit 122 simultaneously turning on the red and the green light sources 61R and 61G and measures the pulse wave data of all the pixels (Step S101). The signal processing circuit 44 stores the measurement results in the storage circuit 46 (refer to FIG. 14) (Step S102). The signal processing circuit 44 then refers to the combination table stored in the storage circuit 46 (Step S103) and selects two pixels in a predetermined combination (Step S104).

The signal processing circuit 44 further refers to the SpO2 calculation parameter table for each combination of the two pixels selected at Step S104 (Step S105). The signal processing circuit 44 reads the data of the two pixels selected at Step S104 from the storage circuit 46 and calculates the blood oxygen saturation level SpO2 using the data of the two pixels (Step S106). The signal processing circuit 44 stores the result of the calculation of the blood oxygen saturation level SpO2 in the storage circuit 46 (Step S107).

Then, the signal processing circuit 44 determines whether calculations have been performed for all the pixel combinations (Step S108). If the result of the determination at Step S108 indicates that calculations have been performed for all combinations of the optical sensors (Yes at Step S108), the process proceeds to Step S109, where the signal processing circuit 44 calculates the average value of the blood oxygen saturation levels SpO2 for all combinations (Step S109). The signal processing circuit 44 outputs the calculated value of the blood oxygen saturation level SpO2 (Step S110) and ends the process.

If, in contrast, the result of the determination at Step S108 indicates that calculations have not been performed for all combinations of the optical sensors (No at Step S108), that is, if combinations for which calculations have not been performed are present, the process returns to Step S103, where the signal processing circuit 44 continues the process. Through the process described above, using the multiple pixels, the blood oxygen saturation level SpO2 can be calculated for each combination of the pixels, and the average value of the results of the calculations can be calculated. The data read from the storage circuit 46 at Step S106 may be temporarily held in a buffer (not illustrated), for example, and used again for the next calculation of the blood oxygen saturation level SpO2. For example, if the data of the pixel Pix1 used in the calculation of the blood oxygen saturation level $SpO2_1$ in FIG. 10 is held in the buffer, the data can be used again in the next calculation of the blood oxygen saturation level $SpO2_2$. This operation can make the processing time of the calculation shorter than in the case of reading the data of the two pixels from the storage circuit 46 each time.

Modification of Arrangement

Figure 12:
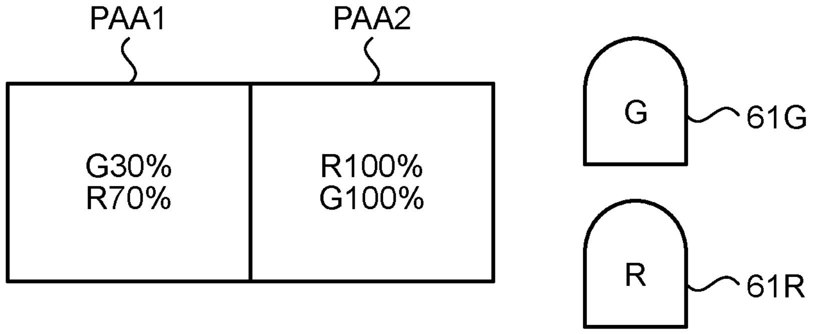
FIG. 12 is a diagram illustrating a modification of an arrangement of the optical sensors and light sources.

FIG. 12 is a diagram illustrating a modification of arrangement of the optical sensors and the light sources. As illustrated in FIG. 12, the optical sensor PAA1 serving as the first optical sensor and the optical sensor PAA2 serving as the second optical sensor are provided adjacent to each other. For the optical sensors PAA1 and PAA2 adjacent to each other, the green light source 61G serving as the first light source and the red light source 61R serving the second light source are provided at locations closer to the optical sensor PAA2. That is, the green light source 61G and the red light source 61R are provided closer to the optical sensor PAA2 than to the optical sensor PAA1. In this case, the second optical sensor PAA2 is provided at a location interposed between the optical sensor PAA1 and the green light source 61G serving as the first light source. The optical sensor PAA2 is provided at a location interposed between the optical sensor PAA1 and the red light source 61R serving as the second light source. The optical sensor PAA1 may be the pixel Pix1, and the optical sensor PAA2 may be the pixel Pix2. The following describes a case where the optical sensors PAA1 and PAA2 are provided, in FIG. 12.

As described above, when the distance from the red light source 61R to the optical sensor is the same as the distance from the green light source 61G to the optical sensor, the intensity of the red light detected at the optical sensor is greater than that of the green light as the distance between the red and the green light sources 61R and 61G and the optical sensor is longer. Therefore, in the light detected at the optical sensor PAA2 located closer to the red and the green light sources 61R and 61G, for example, the green light (G) is detected to be 100%, and the red light (R) is detected to be 100%. In contrast, in the light detected at the optical sensor PAAl located farther from the red and the green light sources 61R and 61G, for example, the green light (G) is detected to be 30%, and the red light (R) is detected to be 70%. Thus, even when the optical sensors are provided at the same distance from the red and the green light sources 61R and 61G, the green light (G) component and the red light (R) component do not have the same ratio in the light detected at the two optical sensors. Therefore, even when the light sources and optical sensors are arranged as illustrated in FIG. 12, the value of the blood oxygen saturation level SpO2 can be calculated based on the detection value of the optical sensor by simultaneously turning on the red and the green light sources 61R and 61G. In this case, the value of the blood oxygen saturation level SpO2 can be calculated using the Expressions (1) and (2) given above, if the coefficients "a" and "b" have been determined in advance based on the actual measurement values.

As described above, the optical sensors may be planarly arranged in the vertical and horizontal directions to form a detection area for detecting light. The following describes in more detail the embodiment when using such a detection area.

Figure 13:
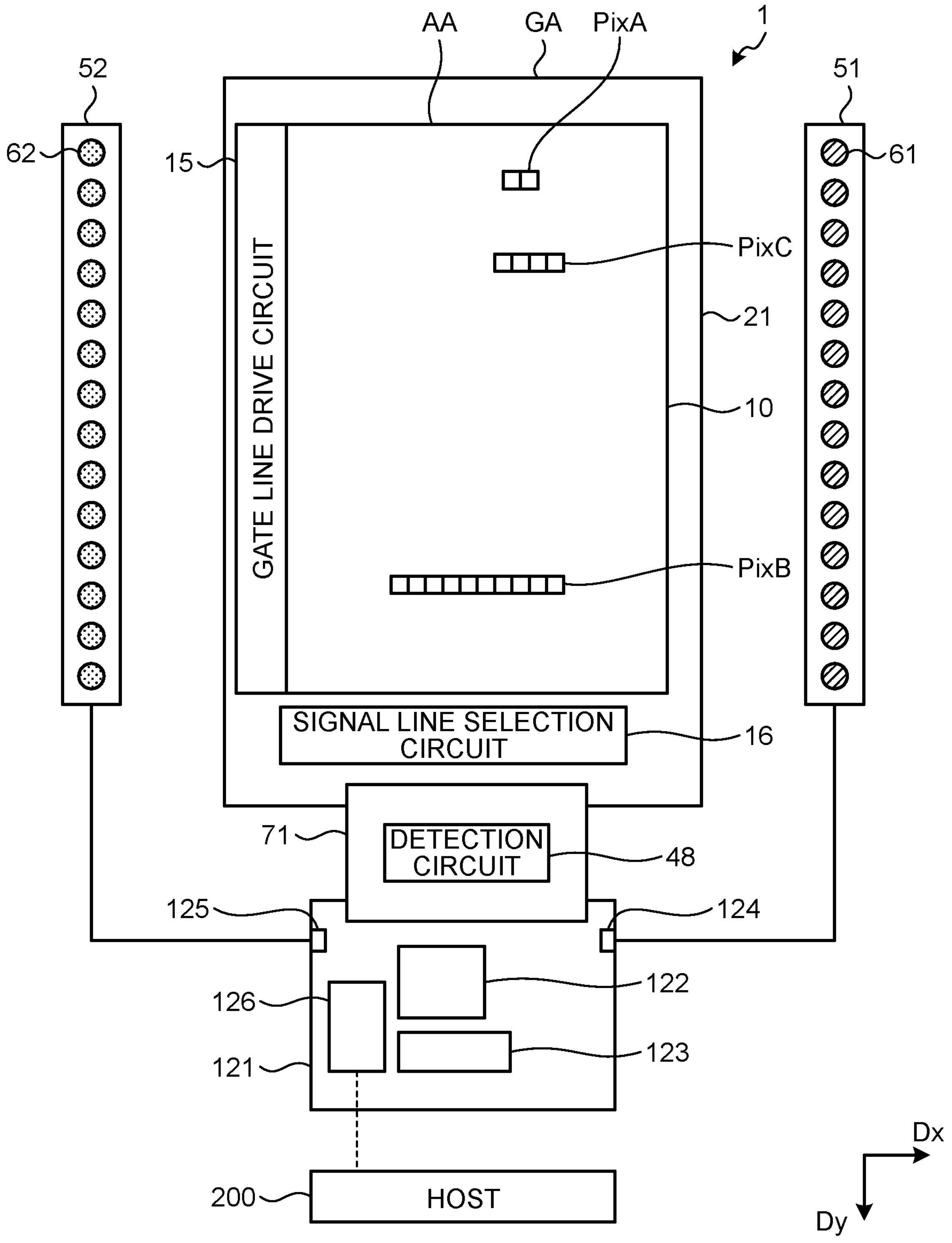
FIG. 13 is a plan view illustrating a detection device according to an embodiment of the present disclosure.

FIG. 13 is a plan view illustrating a detection device according to the embodiment. As illustrated in FIG. 13, a detection device 1 includes a sensor base member 21, a sensor area 10, a gate line drive circuit 15, a signal line selection circuit 16, a detection circuit 48, the control circuit 122, a power supply circuit 123, a plurality of first light sources 61, and a plurality of second light sources 62. The first light sources 61 correspond to the green light source 61G, and the second light sources 62 correspond to the red light source 61R. Two pixels included in the sensor area 10, for example, PixA, correspond to the optical sensors PAA1 and PAA2 in FIG. 3. Ten pixels included in the sensor area 10, for example, PixB, correspond to the pixels Pix1 to Pix10 in FIG. 8. Four pixels included in the sensor area 10, for example, PixC, correspond to the pixels Pix1 to Pix4 in FIG. 9. FIG. 13 illustrates an example in which a first light source base member 51 is provided with the first light sources 61 and a second light source base member 52 is provided with the second light sources 62. However, the arrangement of the first and the second light sources 61 and 62 illustrated in FIG. 13 is merely exemplary, and can be changed as appropriate. For example, the first and the second light sources 61 and 62 may be arranged on the first light source base member 51, as described with reference to FIG. 12.

The detection device 1 is electrically coupled to a host 200. The host 200 is, for example, a higher-level control device for an apparatus (not illustrated) to which the detection device 1 is applied. The host 200 performs a predetermined biometric information acquisition process based on data output from the detection device 1.

The sensor base member 21 is electrically coupled to a control substrate 121 through a flexible printed circuit board 71. The flexible printed circuit board 71 is provided with the detection circuit 48. The control substrate 121 is provided with the control circuit 122, the power supply circuit 123, and an output circuit 126.

The control circuit 122 is, for example, a control integrated circuit (IC) that outputs logic control signals. The control circuit 122 may be, for example, a programmable logic device (PLD) such as a field-programmable gate array (FPGA).

The control circuit 122 supplies control signals to the sensor area 10, the gate line drive circuit 15, and the signal line selection circuit 16 to control a detection operation of the sensor area 10. The control circuit 122 also supplies control signals to the first and the second light sources 61 and 62 to control lighting and non-lighting of the first and the second light sources 61 and 62.

The power supply circuit 123 supplies voltage signals including, for example, a sensor power supply potential VDDSNS (refer to FIG. 17) to the sensor area 10, the gate line drive circuit 15, and the signal line selection circuit 16. The power supply circuit 123 also supplies a power supply voltage to the first and the second light sources 61 and 62.

The output circuit 126 is, for example, a Universal Serial Bus (USB) controller IC, and controls communication between the control circuit 122 and the host 200.

The sensor base member 21 has a detection area AA and a peripheral area GA. The detection area AA is an area provided with a plurality of optical sensors PD (refer to FIG. 17) included in the sensor area 10. The peripheral area GA is an area between the outer perimeter of the detection area AA and the ends of the sensor base member 21, and is an area not provided with the optical sensors PD.

The gate line drive circuit 15 and the signal line selection circuit 16 are provided in the peripheral area GA. Specifically, the gate line drive circuit 15 is provided in an area extending along a second direction Dy in the peripheral area GA. The signal line selection circuit 16 is provided in an area extending along the first direction Dx in the peripheral area GA, and is provided between the sensor area 10 and the detection circuit 48.

The first direction Dx is one direction in a plane parallel to the sensor base member 21. The second direction Dy is one direction in the plane parallel to the sensor base member 21, and is a direction orthogonal to the first direction Dx. The second direction Dy may non-orthogonally intersect the first direction Dx. A third direction Dz is a direction orthogonal to the first direction Dx and the second direction Dy, and is a direction normal to the sensor base member 21.

The first light sources 61 are provided on the first light source base member 51, and are arranged along the second direction Dy. The second light sources 62 are provided on the second light source base member 52, and are arranged along the second direction Dy. The first light source base member 51 and the second light source base member 52 are electrically coupled, through terminals 124 and 125 provided on the control substrate 121, to the control circuit 122 and the power supply circuit 123.

For example, inorganic light-emitting diodes (LEDs) or organic electroluminescent (EL) diodes (organic light-emitting diodes (OLEDs)) are used as the first and the second light sources 61 and 62. The first and the second light sources 61 and 62 emit first light and second light, respectively, having different wavelengths.

The first light emitted from the first light sources 61 is reflected, for example, on a surface of an object to be detected, such as a finger Fg (refer to FIG. 25) or a wrist of a subject of examination, and is incident on the sensor area 10. As a result, the sensor area 10 can detect a fingerprint by detecting a shape of asperities on the surface of the finger Fg or the like. The second light emitted from the second light sources 62 is, for example, reflected in the finger Fg or the like, or transmitted through the finger Fg or the like, and is incident on the sensor area 10. As a result, the sensor area 10 can detect information on a living body in the finger, the wrist, and the like of the subject of examination. Examples of the information on the living body include pulse waves, pulsation, and a vascular image of the subject of examination. That is, the detection device 1 may be configured as a fingerprint detection device to detect the fingerprint or a vein detection device to detect a vascular pattern of, for example, veins.

The first light has a wavelength of 490 nm to 550 nm, and the second light has a wavelength of 640 nm to 770 nm. In this case, the first light is, for example, green visible light (green light), and the second light is, for example, red visible light (red light). The sensor area 10 can detect a blood oxygen level in addition to the pulse waves, the pulsation, and the vascular image as the information on the living body based on the first light emitted from the first light sources 61 and the second light emitted from the second light sources 62. Thus, the detection device 1 includes the first and the second light sources 61 and 62, and performs the detection based on the first light and the detection based on the second light, and thereby can detect the various types of information on the living body.

Figure 14:
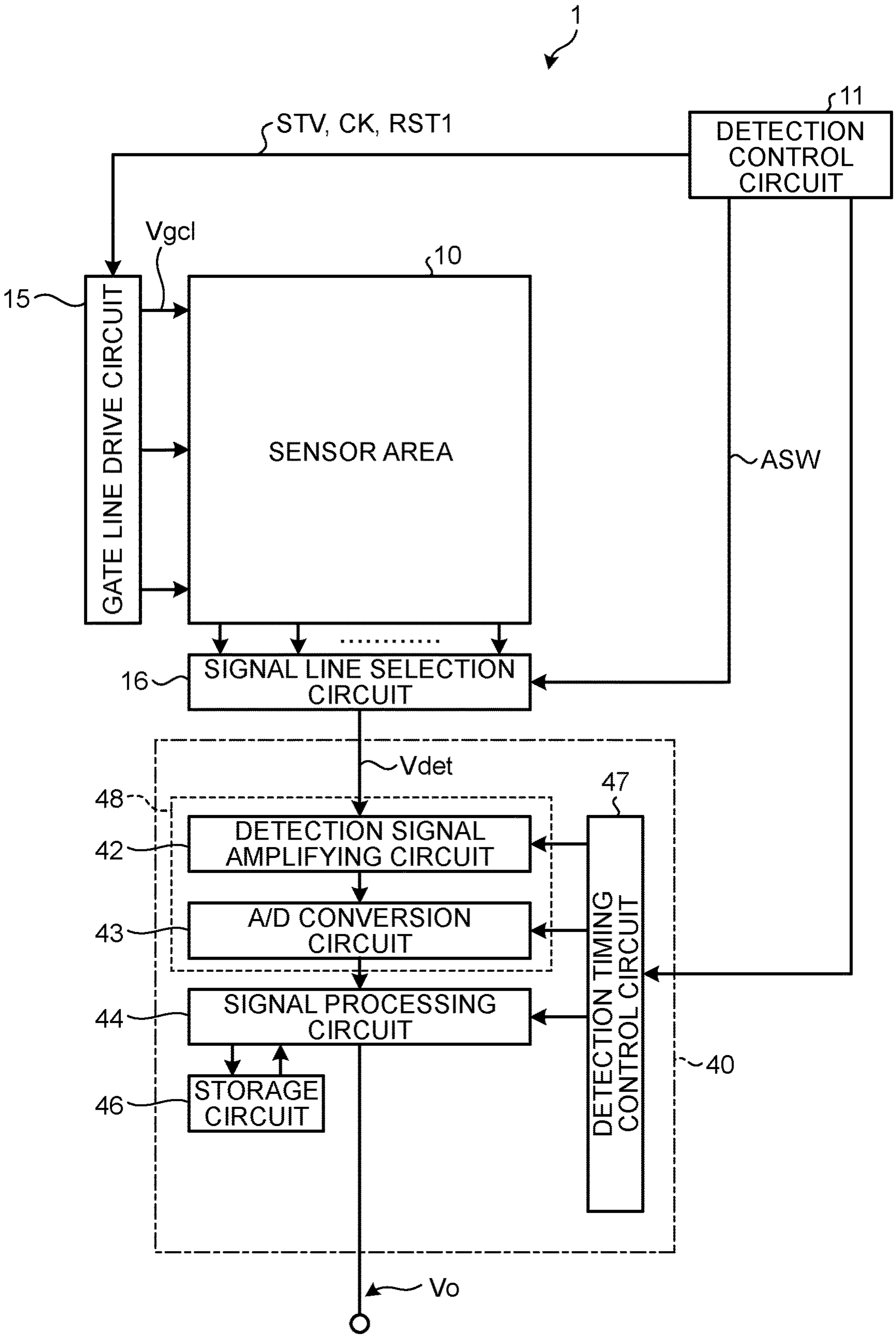
FIG. 14 is a block diagram illustrating a configuration example of the detection device according to the embodiment.

FIG. 14 is a block diagram illustrating a configuration example of the detection device according to the embodiment. As illustrated in FIG. 14, the detection device 1 further includes a detection control circuit 11 and a detection circuit 40.

The sensor area 10 includes the optical sensors PD. Each of the optical sensors PD included in the sensor area 10 is an organic photodiode (OPD), and outputs an electrical signal corresponding to light emitted thereto as a detection signal Vdet to the signal line selection circuit 16. The sensor area 10 performs the detection according to a gate drive signal Vgcl supplied from the gate line drive circuit 15.

The detection control circuit 11 is a circuit that supplies respective control signals to the gate line drive circuit 15, the signal line selection circuit 16, and the detection circuit 40 to control operations of these circuits. The detection control circuit 11 supplies various control signals including, for example, a start signal STV, a clock signal CK, and a reset signal RST1 to the gate line drive circuit 15. The detection control circuit 11 also supplies various control signals including, for example, a selection signal ASW to the signal line selection circuit 16. The detection control circuit 11 also supplies various control signals to the first and the second light sources 61 and 62 to control the lighting and the non-lighting of each group of the first and the second light sources 61 and 62.

The gate line drive circuit 15 is a circuit that drives a plurality of gate lines GCL (refer to FIG. 15) based on the various control signals. The gate line drive circuit 15 sequentially or simultaneously selects the gate lines GCL, and supplies the gate drive signals Vgcl to the selected gate lines GCL. Through this operation, the gate line drive circuit 15 selects the optical sensors PD coupled to the gate lines GCL.

Figure 15:
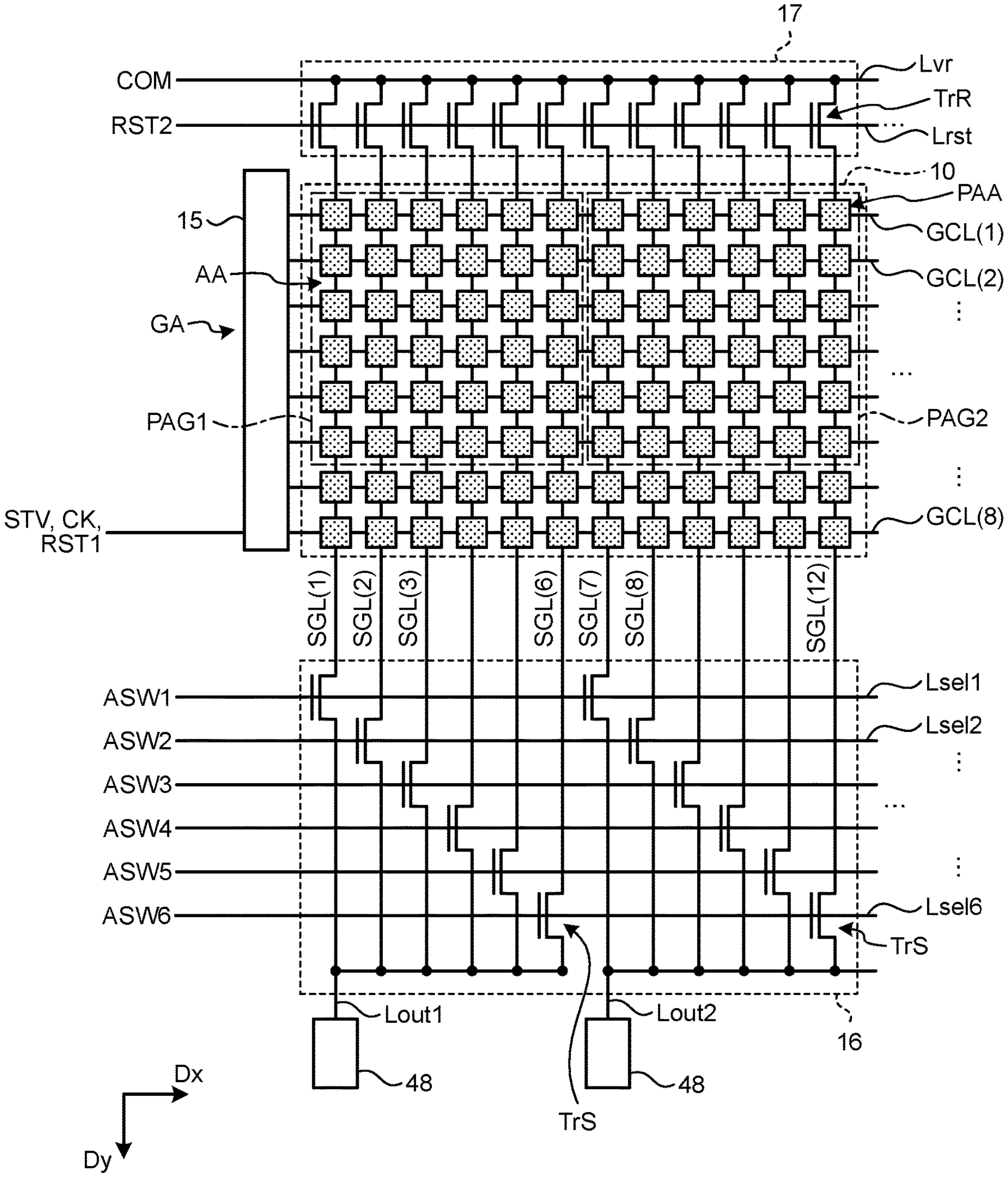
FIG. 15 is a circuit diagram illustrating the detection device.

The signal line selection circuit 16 is a switch circuit that sequentially or simultaneously selects a plurality of signal lines SGL (refer to FIG. 15). The signal line selection circuit 16 is, for example, a multiplexer. The signal line selection circuit 16 electrically couples the selected signal lines SGL to the detection circuit 48 based on the selection signal ASW supplied from the detection control circuit 11. By this operation, the signal line selection circuit 16 outputs the detection signal Vdet of the optical sensor PD to the detection circuit 40.

The detection circuit 40 includes the detection circuit 48, the signal processing circuit 44, the storage circuit 46, and a detection timing control circuit 47. The detection timing control circuit 47 performs control to cause the detection circuit 48 and the signal processing circuit 44 to operate in synchronization with each other based on a control signal supplied from the detection control circuit 11.

The detection circuit 48 generates a detection value of each of the optical sensors PD based on the detection signal of the optical sensor PD output from the sensor area 10. The detection circuit 48 is, for example, an analog front-end (AFE) circuit.

The detection circuit 48 is a signal processing circuit having functions of at least a detection signal amplifying circuit 42 and an analog-to-digital (A/D) conversion circuit 43. The detection signal amplifying circuit 42 amplifies the detection signal Vdet. The A/D conversion circuit 43 converts an analog signal output from the detection signal amplifying circuit 42 into a digital signal.

In the present disclosure, the control circuit 122 includes the signal processing circuit 44 and the storage circuit 46.

The signal processing circuit 44 acquires biometric data for generating the information on the living body based on the detection values of the optical sensors PD output from the detection circuit 48. In the present disclosure, the information on the living body includes the pulse waves acquired using the green light and the red light.

The storage circuit 46 temporarily stores therein signals processed by the signal processing circuit 44. In the present disclosure, the storage circuit 46 also stores therein information on a biometric data acquisition area that is set in a biometric data acquisition area setting process (to be described later) when the signal processing circuit 44 acquires the biometric data, and stores therein various types of setting information. In an aspect of the present disclosure, the storage circuit 46 may include, for example, a random-access memory (RAM), a read-only memory (ROM), and an electrically erasable programmable read-only memory (EEPROM). The storage circuit 46 may be a register circuit, for example.

The following describes a circuit configuration example of the detection device 1. FIG. 15 is a circuit diagram illustrating the detection device. As illustrated in FIG. 15, the sensor area 10 has a plurality of partial detection areas PAA arranged in a matrix having a row-column configuration. Each of the partial detection areas PAA is provided with the optical sensor PD.

The gate lines GCL extend in the first direction Dx, and are each coupled to the partial detection areas PAA arranged in the first direction Dx. A plurality of gate lines GCL(1), GCL(2), . . . , GCL(8) are arranged in the second direction Dy, and are each coupled to the gate line drive circuit 15. In the following description, the gate lines GCL(1), GCL(2), . . . , GCL(8) will each be simply referred to as the gate line GCL when they need not be distinguished from one another. For ease of understanding of the description, FIG. 15 illustrates eight of the gate lines GCL. However, this is merely an example, and M gate lines GCL may be arranged (where M is a natural number, such as 256).

The signal lines SGL extend in the second direction Dy and are each coupled to the optical sensors PD of the partial detection areas PAA arranged in the second direction Dy. A plurality of signal lines SGL(1), SGL(2), . . . , SGL(12) are arranged in the first direction Dx, and are each coupled to the signal line selection circuit 16 and a reset circuit 17. In the following description, the signal lines SGL(1), SGL(2), . . . , SGL(12) will each be simply referred to as the signal line SGL when they need not be distinguished from one another.

For ease of understanding of the description, 12 of the signal lines SGL are illustrated. However, this is merely an example, and N signal lines SGL may be arranged (where N is a natural number, such as 252). In FIG. 15, the sensor area 10 is provided between the signal line selection circuit 16 and the reset circuit 17. The present disclosure is not limited thereto. The signal line selection circuit 16 and the reset circuit 17 may be coupled to ends of the signal lines SGL in the same direction.

The gate line drive circuit 15 receives the various control signals such as the start signal STV, the clock signal CK, and the reset signal RST1 from the control circuit 122 (refer to FIG. 13). The gate line drive circuit 15 sequentially selects the gate lines GCL(1), GCL(2), . . . , GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the partial detection areas PAA arranged in the first direction Dx are selected as detection targets.

The gate line drive circuit 15 may perform different driving for each of detection modes including the detection of a fingerprint and the detection of a plurality of different items of information on the living body (including, for example, the pulse waves, the pulsation, the vascular image, and the blood oxygen level, which are hereinafter called also simply "biometric information"). For example, the gate line drive circuit 15 may collectively drive more than one of the gate lines GCL.

Specifically, the gate line drive circuit 15 simultaneously selects a predetermined number of the gate lines GCL from among the gate lines GCL(1), GCL(2), . . . , GCL(8) based on the control signals. For example, the gate line drive circuit 15 simultaneously selects six gate lines GCL(1) to GCL(6), and supplies thereto the gate drive signals Vgcl. The gate line drive circuit 15 supplies the gate drive signals Vgcl through the selected six gate lines GCL to the first switching elements Tr. By this operation, block units PAG1 and PAG2 each including corresponding ones of the partial detection areas PAA arranged in the first direction Dx and the second direction Dy are each selected as the detection target. The gate line drive circuit 15 collectively drives the predetermined number of the gate lines GCL, and sequentially supplies the gate drive signals Vgcl in units of the predetermined number of the gate lines GCL.

The signal line selection circuit 16 includes a plurality of selection signal lines Lsel, a plurality of output signal lines Lout, and third switching elements TrS. The third switching elements TrS are provided correspondingly to the signal lines SGL. Six signal lines SGL(1), SGL(2), . . . , SGL(6) are coupled to a common output signal line Lout1. Six signal lines SGL(7), SGL(8), . . . , SGL(12) are coupled to a common output signal line Lout2. The output signal lines Lout1 and Lout2 are each coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are coupled to the gates of the respective third switching elements Trs included in one of the signal line blocks. One of the selection signal lines Lsel is coupled to the gates of the third switching elements TrS in the signal line blocks.

Specifically, selection signal lines Lsel1, Lsel2, . . . , Lsel6 are coupled to the third switching elements Trs corresponding to the signal lines SGL(1), SGL(2), . . . , SGL(6), respectively. The selection signal line Lsell is coupled to the third switching element TrS corresponding to the signal line SGL(1) and the third switching element TrS corresponding to the signal line SGL(7). The selection signal line Lsel2 is coupled to the third switching element TrS corresponding to the signal line SGL(2) and the third switching element TrS corresponding to the signal line SGL(8).

The control circuit 122 (refer to FIG. 13) sequentially supplies the selection signal ASW to the selection signal lines Lsel. This operation causes the signal line selection circuit 16 to operate the third switching elements TrS to sequentially select the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs.

The signal line selection circuit 16 may collectively couple more than one of the signal lines SGL to the detection circuit 48. Specifically, the control circuit 122 (refer to FIG. 13) simultaneously supplies the selection signal ASW to the selection signal lines Lsel. The signal line selection circuit 16 operates the third switching elements TrS to select the signal lines SGL (for example, six of the signal lines SGL) in one of the signal line blocks, and couples the signal lines SGL to the detection circuit 48. As a result, signals detected in each of the block units PAG1 and PAG2 are output to the detection circuit 48. In this case, the signals from the partial detection areas PAA (optical sensors PD) included in each of the block units PAG1 and PAG2 are integrated and output to the detection circuit 48.

The detection is performed for each of the block units PAG1 and PAG2 by the operations of the gate line drive circuit 15 and the signal line selection circuit 16. As a result, the strength of the detection signal Vdet obtained by a one-time detection operation increases, so that the sensor sensitivity can be improved.

In the detection device 1 of the present disclosure, the number of the partial detection areas PAA (optical sensors PD) included in each of the block units PAG1 and PAG2 can be changed. Thus, the value of resolution per inch (pixels per inch (ppi), hereinafter, referred to as "definition") can be set depending on the information to be acquired.

For example, the number of the partial detection areas PAA (optical sensors PD) included in each of the block units PAG1 and PAG2 can be relatively reduced. While this setting results in a longer detection time and a lower frame rate (for example, 20 frames per second (fps) or lower), the detection can be performed at a higher definition (for example, at 300 ppi or higher). Hereafter, the term "first mode" denotes a mode of performing the detection at a lower frame rate and a higher definition. By selecting the first mode of performing the detection at a lower frame rate and a higher definition, for example, the fingerprint on the surface of a finger can be acquired at a higher definition.

Alternatively, for example, the number of the partial detection areas PAA (optical sensors PD) included in each of the block units PAG1 and PAG2 can be relatively increased. While this setting results in a lower definition (for example, 50 ppi or lower), the detection can be performed at a higher frame rate (for example, at 100 fps or higher) that allows the detection to be repeatedly performed in a shorter time in one frame. Hereafter, the term "second mode" denotes a mode of performing the detection at a higher frame rate and a lower definition. By selecting the second mode of performing the detection at a higher frame rate and a lower definition, for example, a change in pulse wave with time can be more accurately detected. In the second mode, calculation of a pulse wave velocity, calculation of blood pressure, and the like are enabled by using the pulse waves acquired at a higher frame rate (for example, 1000 fps or higher).

For example, in a case of acquiring the vascular image (vein pattern), the number of the partial detection areas PAA (optical sensors PD) included in each of the block units PAG1 and PAG2 is set to an intermediate value between those of the first mode and the second mode. This setting allows the detection to be performed at a medium frame rate that is higher than that of the first mode and lower than that of the second mode (for example, higher than 20 fps and lower than 100 fps) and at a medium definition that is lower than that of the first mode and higher than that of the second mode (for example, higher than 50 ppi and lower than 300 ppi). Hereafter, the term "third mode" denotes a mode of performing the detection at a medium frame rate and a medium definition. The third mode of performing the detection at a medium frame rate and a medium definition is suitable for, for example, acquiring the vascular pattern of veins and the like.

As illustrated in FIG. 15, the reset circuit 17 includes a reference signal line Lvr, a reset signal line Lrst, and fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 17) included in each of the partial detection areas PAA.

Figure 16:
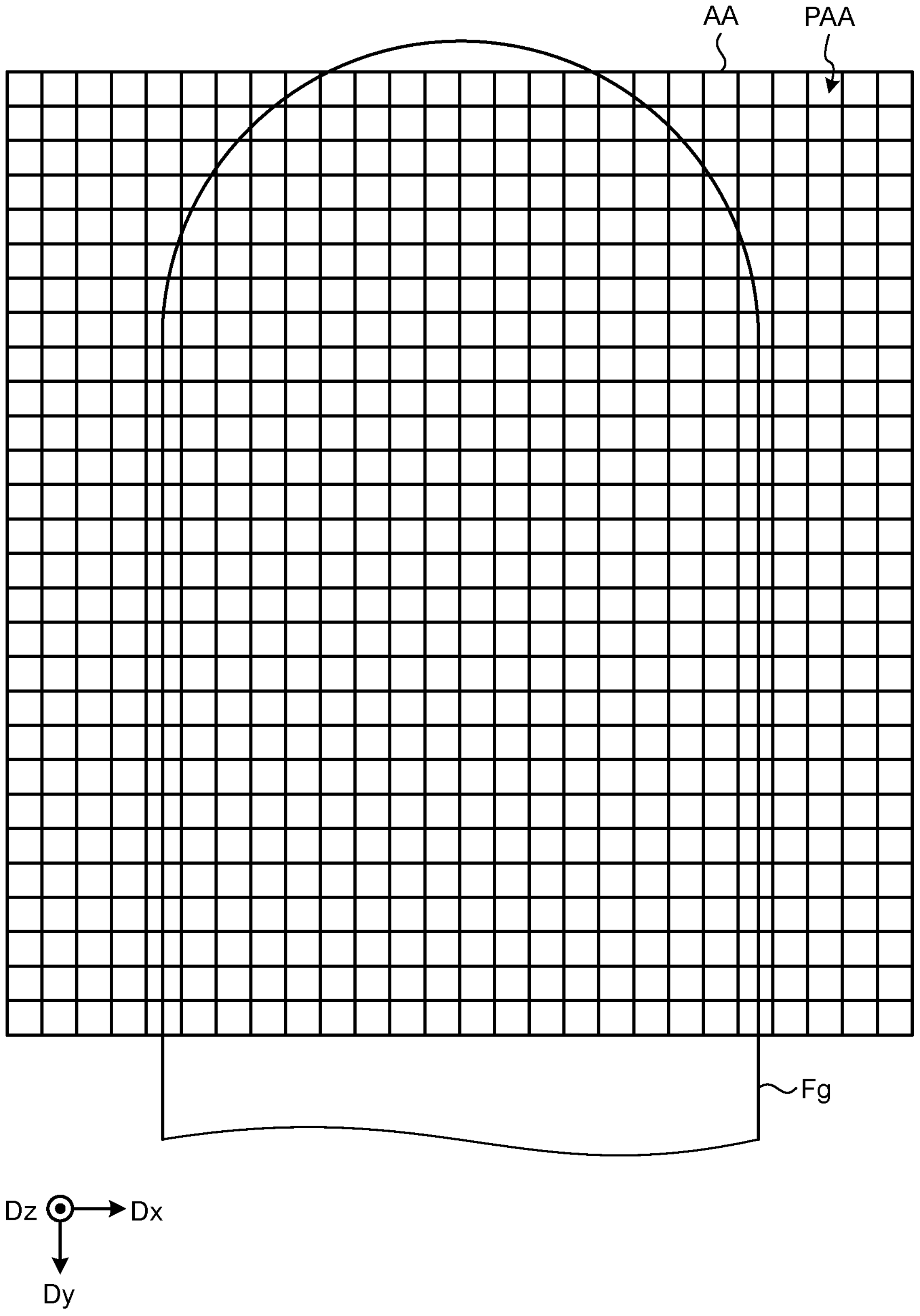
FIG. 16 is a schematic diagram illustrating a positional relation between a detection area of a sensor area and an object to be detected.

FIG. 16 is a schematic diagram illustrating a positional relation between the detection area of the sensor area and the object to be detected. FIG. 16 illustrates the finger Fg of the subject of examination as the object to be detected. The finger Fg is placed in the detection area AA. The finger Fg is placed covering a portion of the detection area AA. The object to be detected is not limited to the finger Fg of the subject of examination but may be the wrist or the like thereof.

Figure 17:
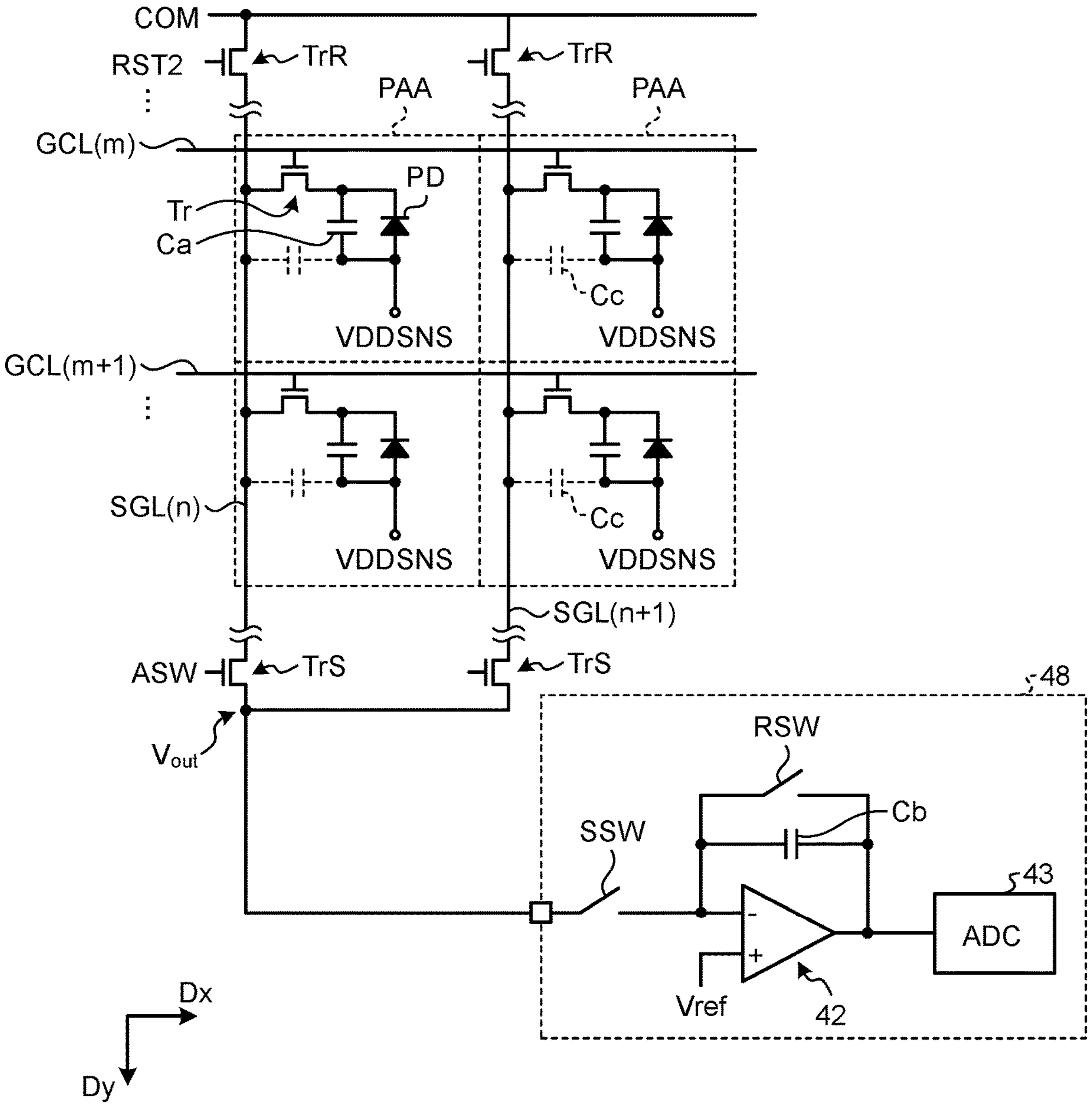
FIG. 17 is a circuit diagram illustrating a plurality of partial detection areas of the detection device according to the embodiment.

FIG. 17 is a circuit diagram illustrating the partial detection areas of the detection device according to the embodiment. FIG. 17 also illustrates a circuit configuration of the detection circuit 48. As illustrated in FIG. 17, each of the partial detection areas PAA includes the optical sensor PD, the capacitive element Ca, and a corresponding one of the first switching elements Tr. The capacitive element Ca is a capacitor (sensor capacitance) generated in the optical sensor PD, and is equivalently coupled in parallel to the optical sensor PD. In addition, signal line capacitance Cc is parasitic capacitance generated on the signal line SGL, and is equivalently provided between the signal line SGL and a node between the anode of the optical sensor PD and one end side of the capacitive element Ca.

FIG. 17 illustrates two gate lines GCL(m) and GCL(m+1) arranged in the second direction Dy among the gate lines GCL. FIG. 17 also illustrates two signal lines SGL(n) and SGL(n+1) arranged in the first direction Dx among the signal lines SGL. The partial detection area PAA is an area surrounded by the gate lines GCL and the signal lines SGL.

Each of the first switching elements Tr is provided correspondingly to the optical sensor PD. The first switching element Tr is formed of a thin-film transistor, and in this example, formed of an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the optical sensor PD and the capacitive element Ca.

The anode of the optical sensor PD is supplied with the sensor power supply potential VDDSNS from the power supply circuit 123. The signal line SGL and the capacitive element Ca are supplied with the reference signal COM that serves as an initial potential of the signal line SGL and the capacitive element Ca from the power supply circuit 123.

When the partial detection area PAA is irradiated with light, a current corresponding to an amount of light flows through the optical sensor PD. As a result, an electric charge is stored in the capacitive element Ca. After the first switching element Tr is turned on, a current corresponding to the electric charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the amount of light received by the optical sensor PD in each of the partial detection areas PAA or signals corresponding to the amounts of light irradiating the optical sensors PD in each of the block units PAG1 and PAG2. Initialization of the light quantities of the first and the second light sources 61 and 62 will be described later.

During a read period Pdet (refer to FIG. 19), a switch SSW of the detection circuit 48 is turned on, and the detection circuit 48 is coupled to the signal lines SGL. The detection signal amplifying circuit 42 of the detection circuit 48 converts a current supplied from the signal lines SGL into a voltage corresponding to the value of the current and amplifies the result. A reference potential (Vref) having a fixed potential is supplied to a non-inverting input terminal (+) of the detection signal amplifying circuit 42, and the signal lines SGL are coupled to an inverting input terminal (−) of the detection signal amplifying circuit 42. In the embodiment, the same signal as the reference signal COM is supplied as the reference potential (Vref) voltage. The detection signal amplifying circuit 42 includes a capacitive element Cb and a reset switch RSW. During a reset period Prst (refer to FIG. 19), the reset switch RSW is turned on, and the electric charge of the capacitive element Cb is reset.

Figure 18A:
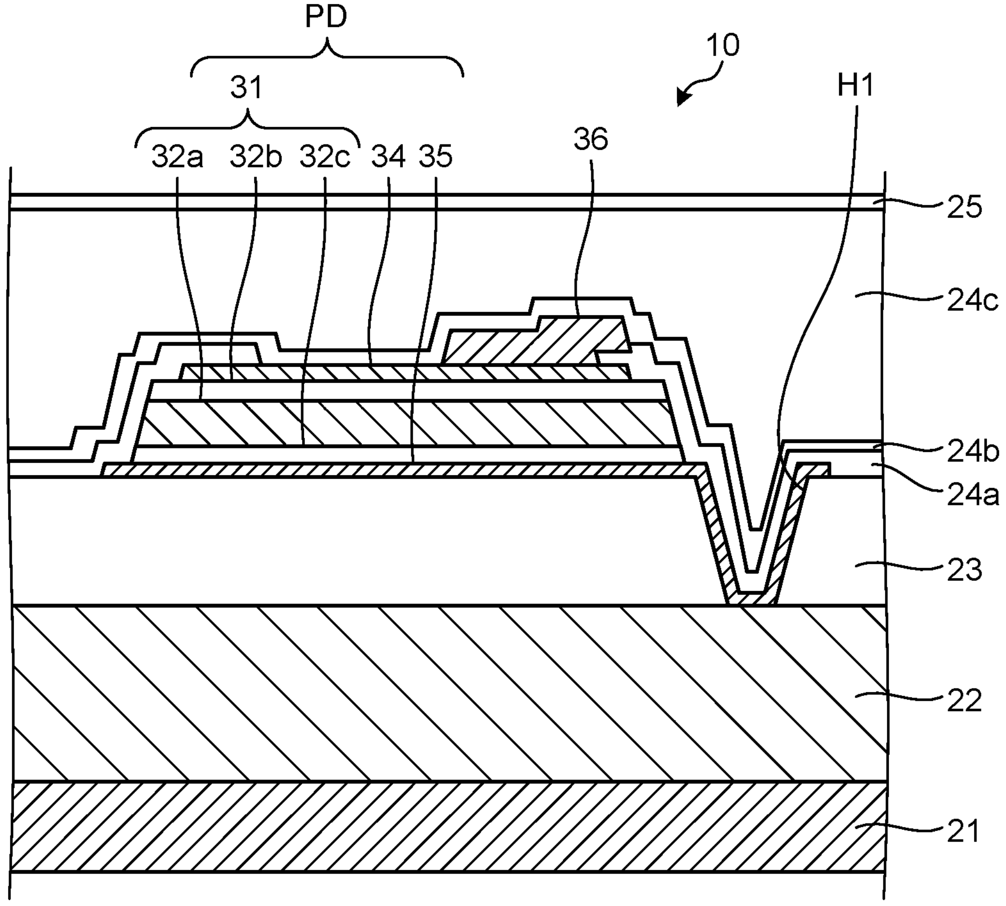
FIG. 18A is a sectional view illustrating a schematic sectional configuration of the sensor area.

The following describes a configuration example of the optical sensor PD. FIG. 18A is a sectional view illustrating a schematic sectional configuration of the sensor area. As illustrated in FIG. 18A, the sensor area 10 includes the sensor base member 21, a TFT layer 22, an insulating layer 23, the optical sensor PD, and insulating layers 24*a*, 24*b*, 24*c*, and 25. The sensor base member 21 is an insulating base member, and is made using, for example, glass or a resin material. The sensor base member 21 is not limited to having a flat plate shape, but may have a curved surface. In this case, the sensor base member 21 may be a film-like resin. The sensor base member 21 has a first surface and a second surface opposite the first surface. The TFT layer 22, the insulating layer 23, the optical sensor PD, and the insulating layers 24 and 25 are stacked in this order on the first surface.

The TFT layer 22 is provided with circuits such as the gate line drive circuit 15 and the signal line selection circuit 16 described above. The TFT layer 22 is also provided with TFTs, such as the first switching elements Tr, and various types of wiring, such as the gate lines GCL and the signal lines SGL. The sensor base member 21 and the TFT layer 22 serve as a drive circuit board that drives the sensor for each predetermined detection area, and are also called a backplane or an array substrate.

The insulating layer 23 is an organic insulating layer, and is provided on the TFT layer 22. The insulating layer 23 is a planarizing layer that planarizes asperities formed by the first switching elements Tr and various conductive layers formed in the TFT layer 22.

The optical sensor PD is provided on the insulating layer 23. The optical sensor PD includes a lower electrode 35, a semiconductor layer 31, and an upper electrode 34, which are stacked in this order.

The lower electrode 35 is provided above the insulating layer 23 and is electrically coupled to the first switching element Tr in the TFT layer 22 through a contact hole H1. The lower electrode 35 is the cathode of the optical sensor PD, and is an electrode for reading the detection signal Vdet. A metal material such as molybdenum (Mo) or aluminum (Al) is used as the lower electrode 35. Alternatively, the lower electrode 35 may be a multilayered film formed by stacking these metal materials. The lower electrode 35 may be formed of, for example, a light-transmitting conductive material such as indium tin oxide (ITO).

The semiconductor layer 31 is formed of amorphous silicon (a-Si). The semiconductor layer 31 includes an i-type semiconductor layer 32*a*, a p-type semiconductor layer 32*b*, and an n-type semiconductor layer 32*c*. The i-type semiconductor layer 32*a*, the p-type semiconductor layer 32*b*, and the n-type semiconductor layer 32*c* constitute a specific example of a photoelectric conversion element. In FIG. 18A, the n-type semiconductor layer 32*c*, the i-type semiconductor layer 32*a*, and the p-type semiconductor layer 32*b* are stacked in this order in a direction orthogonal to a surface of the sensor base member 21. However, the semiconductor layer 31 may have a reversed configuration, that is, the p-type semiconductor layer 32*b*, the i-type semiconductor layer 32*a*, and the n-type semiconductor layer 32*c* may be stacked in this order. The semiconductor layer 31 may be a photoelectric conversion element formed of organic semiconductors.

The a-Si of the n-type semiconductor layer 32*c* is doped with impurities to form an n+ region. The a-Si of the p-type semiconductor layer 32*b* is doped with impurities to form a p+ region. The i-type semiconductor layer 32*a* is, for example, a non-doped intrinsic semiconductor, and has lower conductivity than that of the p-type semiconductor layer 32*b* and the n-type semiconductor layer 32*c*.

The upper electrode 34 is the anode of the optical sensor PD, and is an electrode for supplying the sensor power supply potential VDDSNS to the photoelectric conversion layer. The upper electrode 34 is a light-transmitting conductive layer of, for example, ITO, and is provided so as to be common to all the optical sensors PD.

The insulating layers 24*a* and 24*b* are provided on the insulating layer 23. The insulating layer 24*a* covers the periphery of the upper electrode 34, and is provided with an opening at a location overlapping the upper electrode 34. Coupling wiring 36 is coupled to the upper electrode 34 at a portion of the upper electrode 34 not provided with the insulating layer 24*a*. The insulating layer 24*b* is provided on the insulating layer 24*a* covering the upper electrode 34 and the coupling wiring 36. The insulating layer 24*c* serving as a planarizing layer is provided on the insulating layer 24*b*. The insulating layer 25 is provided on the insulating layer 24*c*. However, the insulating layer 25 need not be provided.

Figure 18B:
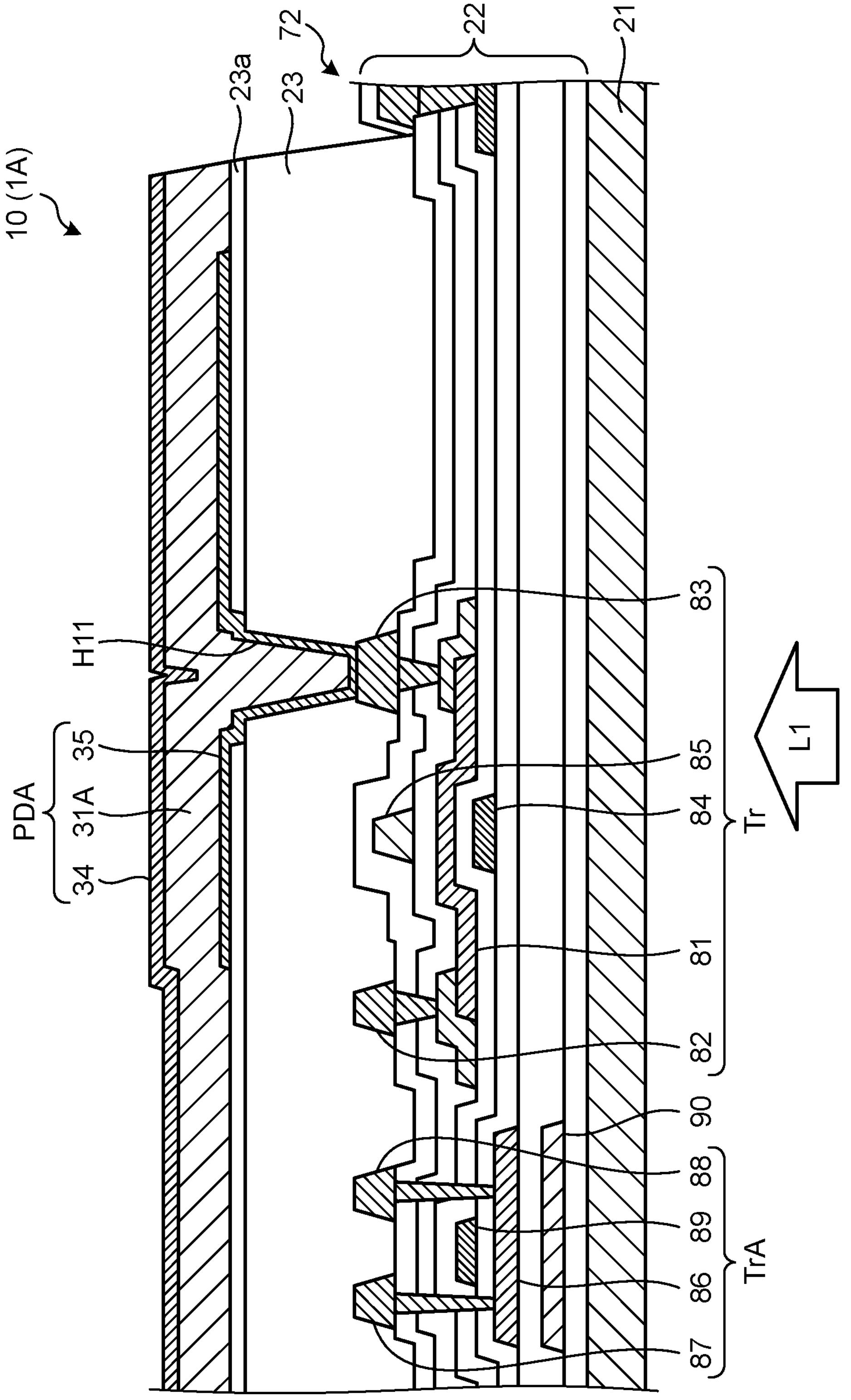
FIG. 18B is a sectional view illustrating a schematic sectional configuration of the sensor area of a detection device according to a modification.

FIG. 18B is a sectional view illustrating a schematic sectional configuration of the sensor area of a detection device according to a modification. As illustrated in FIG. 18B, in a detection device 1A of the modification, an optical sensor PDA is provided above an insulating layer 23*a*. The insulating layer 23*a* is an inorganic insulating layer provided covering the insulating layer 23, and is formed of, for example, silicon nitride (SiN). The optical sensor PDA includes a photoelectric conversion layer 31A, the lower electrode 35 (cathode electrode), and the upper electrode 34 (anode electrode). The lower electrode 35, the photoelectric conversion layer 31A, and the upper electrode 34 are stacked in this order in a direction orthogonal to the first surface S1 of the sensor base member 21.

The photoelectric conversion layer 31A changes in characteristics (for example, voltage-current characteristics and resistance value) depending on light emitted thereto. An organic material is used as a material of the photoelectric conversion layer 31A. Specifically, as the photoelectric conversion layer 31A, low-molecular-weight organic materials can be used, such as fullerene ($C_{60}$), phenyl-$C_{61}$-butyric acid methyl ester (PCBM), copper phthalocyanine (CuPc), fluorinated copper phthalocyanine ($F_{16}CuPc$), 5,6,11,12-tetraphenyltetracene (rubrene), and perylene diimide (PDI) (derivative of perylene).

The photoelectric conversion layer 31A can be formed by a vapor deposition process (dry process) using the low-molecular-weight organic materials listed above. In this case, the photoelectric conversion layer 31A may be, for example, a multilayered film of CuPc and $F_{16}CuPc$, or a multilayered film of rubrene and $C_{60}$. The photoelectric conversion layer 31A can also be formed by a coating process (wet process). In this case, the photoelectric conversion layer 31A is made using a material obtained by combining the above-listed low-molecular-weight organic materials with high-molecular-weight organic materials. As the high-molecular-weight organic materials, for example, poly (3-hexylthiophene) (P3HT) and F8-alt-benzothiadiazole (F8BT) can be used. The photoelectric conversion layer 31A can be a film in the state of a mixture of P3HT and PCBM, or a film in the state of a mixture of F8BT and PDI.

The lower electrode 35 faces the upper electrode 34 with the photoelectric conversion layer 31A interposed therebetween. A light-transmitting conductive material such as ITO is used as the upper electrode 34. A metal material such as silver (Ag) or aluminum (Al) is used as the lower electrode 35. Alternatively, the lower electrode 35 may be an alloy material containing at least one or more of these metal materials.

By controlling the film thickness of the lower electrode 35, it is possible to form the lower electrode 35 as a light-transmitting transflective electrode. For example, the lower electrode 35 is formed of a thin Ag film having a thickness of 10 nm, and can have light transmittance of approximately 60%. In this case, the optical sensor PDA can detect light emitted from both sides of the sensor base member 21, for example, both light L1 emitted from the first surface S1 side and light emitted from the second surface S2 side.

Although not illustrated in FIG. 18B, the insulating layer 24 may be provided covering the upper electrode 34. The insulating layer is a passivation film, and is provided to protect the optical sensor PDA.

As illustrated in FIG. 18B, the TFT layer 22 is provided with the first switching element Tr electrically coupled to the optical sensor PDA. The first switching element Tr includes a semiconductor layer 81, a source electrode 82, a drain electrode 83, and gate electrodes 84 and 85. The lower electrode 35 of the optical sensor PDA is electrically coupled to the drain electrode 83 of the first switching element Tr through a contact hole H11 provided in the insulating layers 23 and 23*a*.

The first switching element Tr has what is called a dual-gate structure provided with the gate electrodes 84 and 85 on the upper and lower sides of the semiconductor layer 81. However, the first switching element Tr is not limited to having this structure but may have a top-gate structure or a bottom-gate structure.

FIG. 18B schematically illustrates a second switching element TrA and a terminal 72 that are provided in the peripheral area GA. The second switching element TrA is, for example, a switching element provided in the gate line drive circuit 15 (refer to FIG. 13). The second switching element TrA includes a semiconductor layer 86, a source electrode 87, a drain electrode 88, and a gate electrode 89. The second switching element TrA has what is called a top-gate structure provided with the gate electrode 89 on the upper side of the semiconductor layer 86. A light-blocking layer 90 is provided between the semiconductor layer 86 and the sensor base member 21 on the lower side of the semiconductor layer 86. However, the second switching element TrA is not limited to having this structure, but may have a bottom-gate structure or a dual-gate structure.

The semiconductor layer 81 of the first switching element Tr is provided in a layer different from that of the semiconductor layer 86 of the second switching element TrA. The semiconductor layer 81 of the first switching element Tr is formed of an oxide semiconductor, for example. The semiconductor layer 86 of the second switching element TrA is formed of polysilicon, for example.

Figure 19:
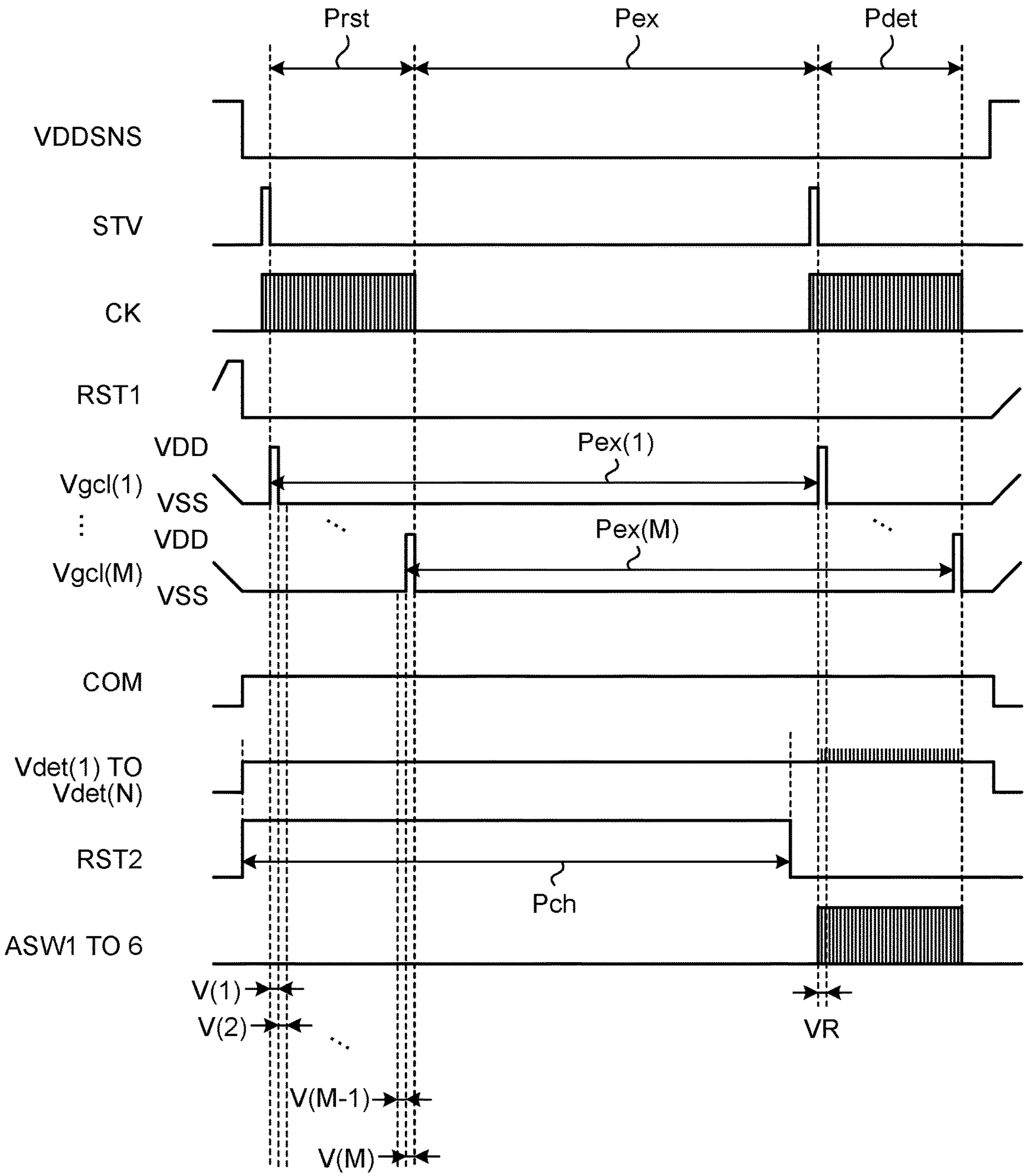
FIG. 19 is a timing waveform diagram illustrating an operation example of the detection device.
Figure 20:
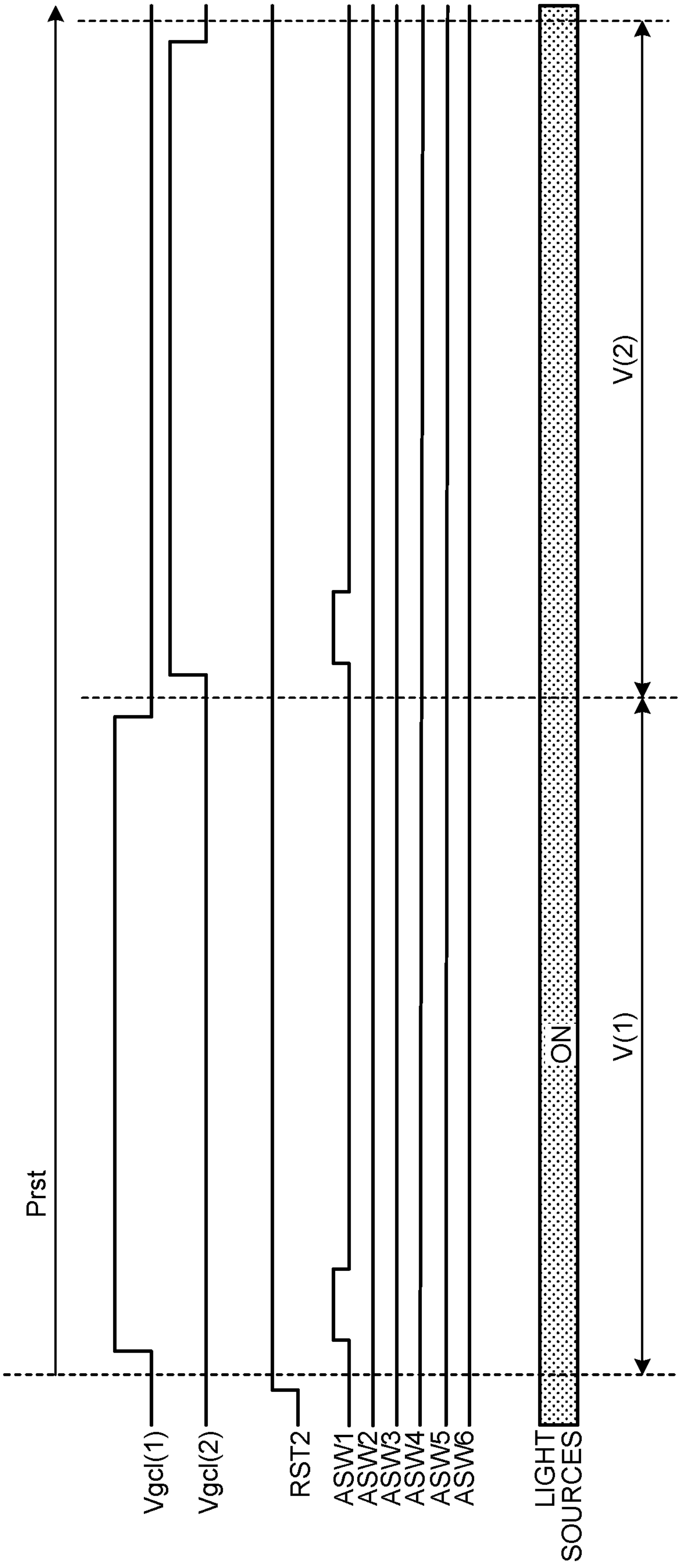
FIG. 20 is a timing waveform diagram illustrating an operation example during a reset period in FIG. 19.
Figure 21:
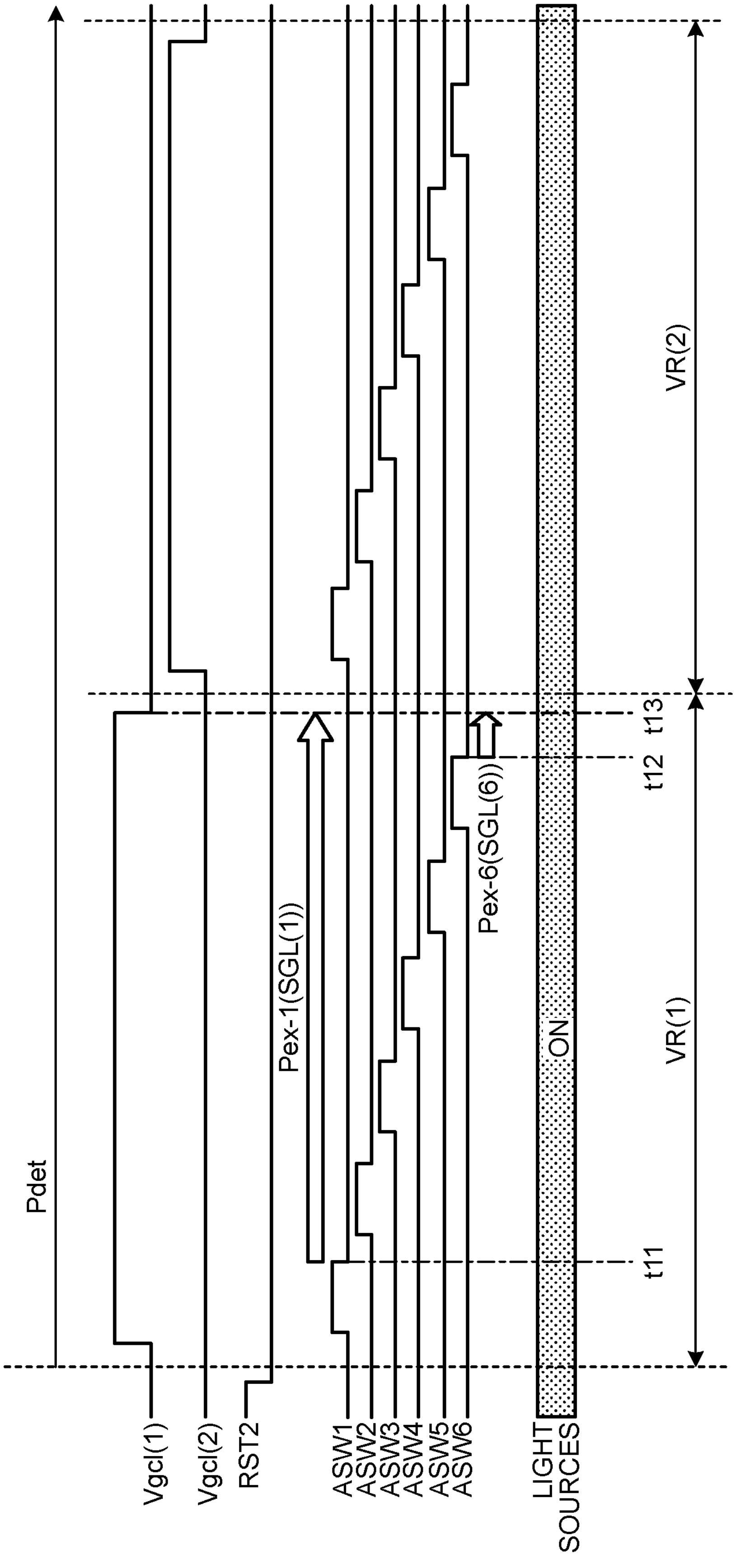
FIG. 21 is a timing waveform diagram illustrating an operation example during a read period in FIG. 19.
Figure 22:
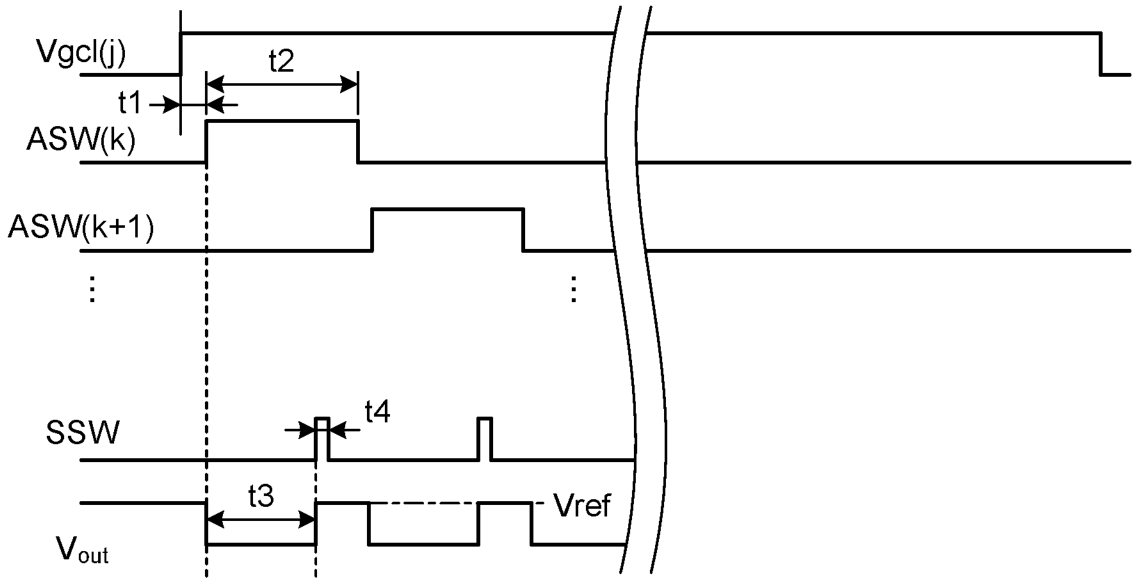
FIG. 22 is a timing waveform diagram illustrating an operation example during a drive period of one gate line included in a row read period in FIG. 19.
Figure 23:
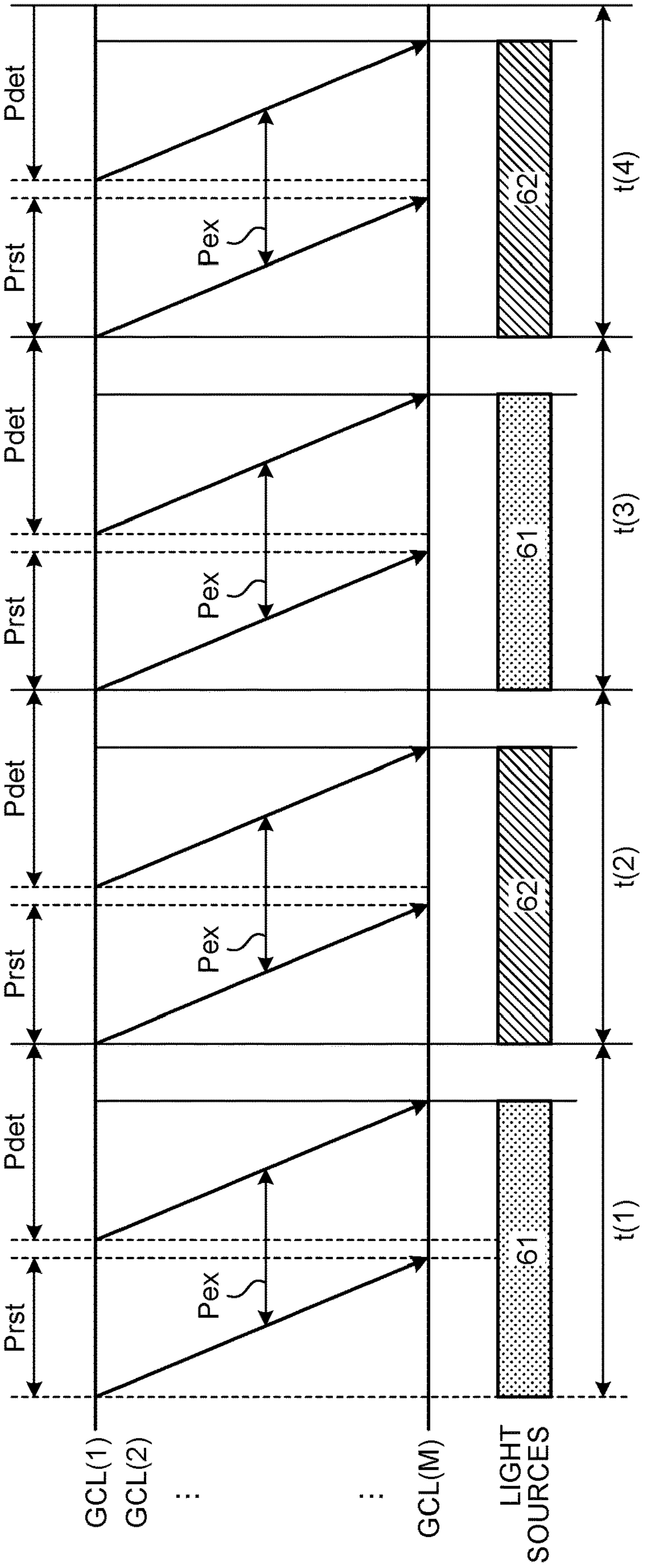
FIG. 23 is an explanatory diagram for explaining a relation between driving of the sensor area and lighting operations of light sources according to the comparative example.
Figure 24:
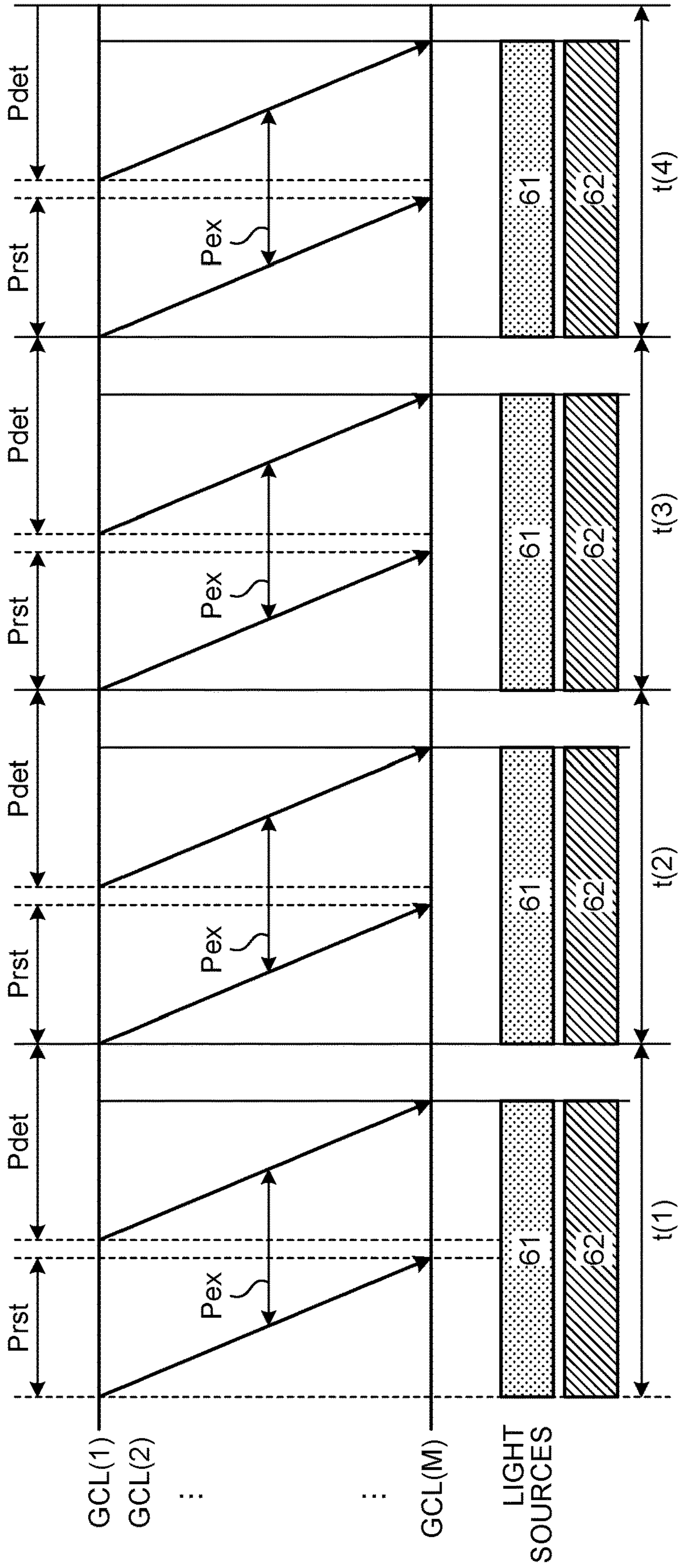
FIG. 24 is an explanatory diagram for explaining the relation between the driving of the sensor area and lighting operations of the light sources in the detection device of the present disclosure.

The following describes an operation example of the detection device 1. FIG. 19 is a timing waveform diagram illustrating the operation example of the detection device. FIG. 20 is a timing waveform diagram illustrating an operation example during the reset period in FIG. 19. FIG. 21 is a timing waveform diagram illustrating an operation example during the read period in FIG. 19. FIG. 22 is a timing waveform diagram illustrating an operation example during a drive period of one gate line included in a row read period VR in FIG. 19. FIGS. 23 and 24 are explanatory diagrams each for explaining a relation between the driving of the sensor area and the lighting operations of the light sources in the detection device.

As illustrated in FIG. 19, the detection device 1 has the reset period Prst, an exposure period Pex, and the read period Pdet. The power supply circuit 123 supplies the sensor power supply potential VDDSNS to the anode of the optical sensor PD over the reset period Prst, the exposure period Pex, and the read period Pdet. The sensor power supply potential VDDSNS is a signal for applying a reverse bias between the anode and the cathode of the optical sensor PD. For example, the reference signal COM of substantially 0.75 V is applied to the cathode of the optical sensor PD, and the sensor power supply potential VDDSNS of substantially −1.25 V is applied to the anode thereof. As a result, a reverse bias of substantially 2.0 V is applied between the anode and the cathode. The control circuit 122 sets the reset signal RST2 to "H", and then, supplies the start signal STV and the clock signal CK to the gate line drive circuit 15 to start the reset period Prst. During the reset period Prst, the control circuit 122 supplies the reference signal COM to the reset circuit 17, and uses the reset signal RST2 to turn on the fourth switching elements TrR for supplying a reset voltage. This operation supplies the reference signal COM as the reset voltage to each of the signal lines SGL. The reference signal COM is set to, for example, 0.75 V.

During the reset period Prst, the gate line drive circuit 15 sequentially selects the gate lines GCL based on the start signal STV, the clock signal CK, and the reset signal RST1. The gate line drive circuit 15 sequentially supplies gate drive signals Vgcl {Vgcl(1), . . . , Vgcl(M)} to the gate lines GCL. Each of the gate drive signals Vgcl has a pulsed waveform having a power supply voltage VDD serving as a high-level voltage and a power supply voltage VSS serving as a low-level voltage. In FIG. 19, M gate lines GCL(where M is, for example, 256) are provided, and the gate drive signals Vgcl(1), . . . , Vgcl(M) are sequentially supplied to the respective gate lines GCL. Thus, the first switching elements Tr are sequentially brought into a conducting state and supplied with the reset voltage on a row-by-row basis. For example, a voltage of 0.75 V of the reference signal COM is supplied as the reset voltage.

Specifically, as illustrated in FIG. 20, the gate line drive circuit 15 supplies the gate drive signal Vgcl(1) at the high-level voltage (power supply voltage VDD) to the gate line GCL(1) during a period V(1). The control circuit 122 supplies any one of selection signals ASW1, . . . , ASW6 (selection signal ASW1 in FIG. 20) to the signal line selection circuit 16 during a period in which the gate drive signal Vgcl(1) is at the high-level voltage (power supply voltage VDD). This operation couples the signal line SGL of the partial detection area PAA selected by the gate drive signal Vgcl(1) to the detection circuit 48. As a result, the reset voltage (reference signal COM) is also supplied to coupling wiring between the third switching element TrS and the detection circuit 48.

In the same manner, the gate line drive circuit 15 supplies the gate drive signals Vgcl(2), . . . , Vgcl(M−1), Vgcl(M) at the high-level voltage to gate lines GCL(2), . . . , GCL(M−1), GCL(M) during periods V(2), . . . , V(M−1), (M), respectively.

Thus, during the reset period Prst, the capacitive elements Ca of all the partial detection areas PAA are sequentially electrically coupled to the signal lines SGL, and are supplied with the reference signal COM. As a result, the capacitance of the capacitive elements Ca is reset. The capacitance of the capacitive elements Ca of some of the partial detection areas PAA can be reset by partially selecting the gate lines and the signal lines SGL.

Examples of the method of controlling the exposure include a method of controlling the exposure during non-selection of the gate lines and a method of always controlling the exposure. In the method of controlling the exposure during non-selection of the gate lines, the gate drive signals {Vgcl(1), . . . , Vgcl(M)} are sequentially supplied to all the gate lines GCL coupled to the optical sensors PD serving as the detection targets, and all the optical sensors PD serving as the detection targets are supplied with the reset voltage. Then, after all the gate lines GCL coupled to the optical sensors PD serving as the detection targets are set to a low voltage (the first switching elements Tr are turned off), the exposure starts and the exposure is performed during the exposure period Pex. After the exposure ends, the gate drive signals {Vgcl(1), . . . , Vgcl(M)} are sequentially supplied to the gate lines GCL coupled to the optical sensors PD serving as the detection targets as described above, and reading is performed during the read period Pdet. In the method of always controlling the exposure, the control for performing the exposure is also performed during the reset period Prst and the read period Pdet (the exposure is always controlled). In this case, the actual exposure period Pex(1) starts immediately after the gate drive signal Vgcl(1) supplied to the gate line GCL becomes L, H, and then L during the reset period Prst. The actual exposure periods Pex{(1), . . . , (M)} are not periods during which the light sources emit light but periods during which the electric charges corresponding to the light received by the optical sensors PD are stored in the the respective capacitive elements Ca in the lighting periods of the light sources. The electric charge stored in the capacitive element Ca during the reset period Prst causes a reverse directional current to flow (from the cathode to the anode) through the optical sensor PD due to light irradiation, and the potential difference in the capacitive element Ca decreases. The start timing and the end timing of the actual exposure periods Pex(1), . . . , Pex(M) are different among the partial detection areas PAA corresponding to the respective gate lines GCL. Each of the exposure periods Pex(1), . . . , Pex(M) starts when the gate drive signal Vgcl changes from the power supply voltage VDD serving as the high-level voltage to the power supply voltage VSS serving as the low-level voltage during the reset period Prst. Each of the exposure periods Pex(1), . . . , Pex(M) ends when the gate drive signal Vgcl changes from the power supply voltage VSS to the power supply voltage VDD during the read period Pdet. The lengths of the exposure time of the exposure periods Pex(1), . . . , Pex(M) are equal.

During the exposure periods Pex {(1), . . . , (M)}, a current flows correspondingly to the light received by the optical sensor PD in each of the partial detection areas PAA. As a result, an electric charge is stored in each of the capacitive elements Ca.

At a time before the read period Pdet starts, the control circuit 122 sets the reset signal RST2 to a low-level voltage. This operation stops the operation of the reset circuit 17. The reset signal may be set to a high-level voltage only during the reset period Prst. During the read period Pdet, the gate line drive circuit 15 sequentially supplies the gate drive signals Vgcl(1), . . . , Vgcl(M) to the gate lines GCL in the same manner as during the reset period Prst.

Specifically, as illustrated in FIG. 21, the gate line drive circuit 15 supplies the gate drive signal Vgcl(1) at the high-level voltage (power supply voltage VDD) to the gate line GCL(1) during a row read period VR(1). The control circuit 122 sequentially supplies the selection signals ASW1, . . . , ASW6 to the signal line selection circuit 16 during a period in which the gate drive signal Vgcl(1) is at the high-level voltage (power supply voltage VDD). This operation sequentially or simultaneously couples the signal lines SGL of the partial detection areas PAA selected by the gate drive signal Vgcl(1) to the detection circuit 48. As a result, the detection signal Vdet for each of the partial detection areas PAA is supplied to the detection circuit 48.

In the same manner, the gate line drive circuit 15 supplies the gate drive signals Vgcl(2), . . . , Vgcl(M−1), Vgcl(M) at the high-level voltage to the gate lines GCL(2), . . . , GCL(M−1), GCL(M) during row read periods VR(2), . . . , VR(M−1), VR(M), respectively. That is, the gate line drive circuit 15 supplies the gate drive signal Vgcl to the gate line GCL during each of the row read periods VR(1), VR(2), . . . , VR(M−1), VR(M). The signal line selection circuit 16 sequentially selects the signal lines SGL based on the selection signal ASW in each period in which the gate drive signal Vgcl is set to the high-level voltage. The signal line selection circuit 16 sequentially couples each of the signal lines SGL to the one detection circuit 48. Thus, the detection device 1 can output the detection signals Vdet of all the partial detection areas PAA to the detection circuit 48 during the read period Pdet.

With reference to FIG. 22, the following describes an operation example during the row read period VR that is a period of supplying one gate drive signal Vgcl(j) in FIG. 19. In FIG. 19, the reference numeral of the row read period VR is assigned to the first gate drive signal Vgcl(1). The same also applies to the other gate drive signals Vgcl(2), . . . , Vgcl(M). The index j is any one of the natural numbers 1 to M.

As illustrated in FIGS. 22 and 17, an output (Vout) of each of the third switching elements TrS has been reset to the reference potential (Vref) voltage in advance. The reference potential (Vref) voltage serves as the reset voltage, and is set to 0.75 V, for example. Then, the gate drive signal Vgcl(j) is set to a high level, and the first switching elements Tr of a corresponding row are turned on. Thus, each of the signal lines SGL in each row is set to a voltage corresponding to the electric charge stored in the capacitor (capacitive element Ca) of the partial detection area PAA. After a period t1 elapses from a rising edge of the gate drive signal Vgcl(j), a period t2 starts in which the selection signal ASW(k) is set to a high level. After the selection signal ASW(k) is set to the high level and the third switching element TrS is turned on, the electric charge stored in the capacitor (capacitive element Ca) of the partial detection area PAA coupled to the detection circuit 48 through the third switching element TrS changes the output (Vout) of the third switching element TrS (refer to FIG. 17) to a voltage corresponding to the electric charge stored in the capacitor (capacitive element Ca) of the partial detection area PAA (in a period t3). In the example of FIG. 22, this voltage is reduced from the reset voltage as illustrated in the period t3. Then, after the switch SSW is turned on (in a period t4 during which an SSW signal is set to a high level), the electric charge stored in the capacitor (capacitive element Ca) of the partial detection area PAA moves to the capacitor (capacitive element Cb) of the detection signal amplifying circuit 42 of the detection circuit 48, and the output voltage of the detection signal amplifying circuit 42 is set to a voltage corresponding to the electric charge stored in the capacitive element Cb. At this time, the potential of the inverting input portion of the detection signal amplifying circuit 42 is set to a virtual short-circuit potential of an operational amplifier, and therefore, becomes the reference potential (Vref). The A/D conversion circuit 43 reads the output voltage of the detection signal amplifying circuit 42. In the example of FIG. 22, waveforms of the selection signals ASW(k), ASW(k+1), . . . corresponding to the signal lines SGL of the respective columns are set to a high level to sequentially turn on the third switching elements TrS, and the same operation is sequentially performed to sequentially read the electric charges stored in the capacitors (capacitive elements Ca) of the partial detection areas PAA coupled to the gate line GCL. ASW(k), ASW(k+1), . . . in FIG. 22 are, for example, any of ASW1 to ASW6 in FIG. 21.

Specifically, after the period t4 starts in which the switch SSW is on, the electric charge moves from the capacitor (capacitive element Ca) of the partial detection area PAA to the capacitor (capacitive element Cb) of the detection signal amplifying circuit 42 of the detection circuit 48. At this time, the non-inverting input (+) of the detection signal amplifying circuit 42 is set to the reference potential (Vref) voltage (for example, 0.75 V). As a result, the output (Vout) of the third switching element TrS is also set to the reference potential (Vref) voltage due to the virtual short-circuit between input ends of the detection signal amplifying circuit 42. The voltage of the capacitive element Cb is set to a voltage corresponding to the electric charge stored in the capacitor (capacitive element Ca) of the partial detection area PAA at a location where the third switching element Trs is turned on in response to the selection signal ASW(k). After the output (Vout) of the third switching element TrS is set to the reference potential (Vref) voltage due to the virtual short-circuit, the output of the detection signal amplifying circuit 42 reaches a voltage corresponding to the capacitance of the capacitive element Cb, and this output voltage is read by the A/D conversion circuit 43. The voltage of the capacitive element Cb is, for example, a voltage between two electrodes provided on a capacitor constituting the capacitive element Cb.

The period t1 is 20 μs, for example. The period t2 is 60 μs, for example. The period t3 is 44.7 μs, for example. The period t4 is 0.98 μs, for example.

FIG. 23 is an explanatory diagram for explaining the relation between the driving of the sensor area and the lighting operations of the light sources according to the comparative example. FIG. 23 illustrates a case where the first and the second light sources 61 and 62 are alternately turned on, that is, turned on in a time-division manner in the same manner as in the comparative example (FIG. 2) described above. In the example illustrated in FIG. 23, the reset period Prst, the exposure period Pex, and the read period Pdet are provided for one-frame detection in each of a period t(1), a period t(2), a period t(3), and a period t(4).

In the reset period Prst and the read period Pdet, the gate line drive circuit 15 sequentially scans the gate lines from GCL(1) to GCL(M).

As illustrated in FIG. 23, the detection device 1 executes the reset period Prst, the exposure periods Pex {(1), . . . , (M)}, and the read period Pdet described above in each of the periods t(1), t(2), t(3), and t(4). In the reset period Prst and the read period Pdet, the gate line drive circuit 15 sequentially scans the gate lines from GCL(1) to GCL(M). In the following description, the term "one-frame detection" denotes the detection in each period t, that is, the detection in which the gate lines are scanned from GCL(1) to GCL(M) in the reset period Prst and the read period Pdet and the detection signals Vdet are acquired from the signal lines SGL in the respective columns. FIG. 23 illustrates an example in which the first light sources 61 are on during the periods t(1) and t(3), and the second light sources 62 are on during the periods t(2) and t(4). That is, in the example illustrated in FIG. 23, the control circuit 122 alternately switches between on and off of the first light sources 61 and the second light sources 62 for each one-frame detection.

As illustrated in FIG. 23, in the one-frame detection in the period t(1), the control circuit 122 (detection control circuit 11) causes the first light sources 61 to be on and the second light sources 62 to be off during the exposure period Pex. In the one-frame detection in the period t(2), the control circuit 122 (detection control circuit 11) causes the first light sources 61 to be off and the second light sources 62 to be on during the exposure period Pex. In the same manner, the first light sources 61 are caused to be on and the second light sources 62 are caused to be off during the exposure period Pex in the one-frame detection in the period t(3); and the first light sources 61 are caused to be off and the second light sources 62 are caused to be on during the exposure period Pex in the one-frame detection in the period t(4).

Thus, in the case of the comparative example illustrated in FIG. 23, the first and the second light sources 61 and 62 are controlled to be caused to be on and off in a time-divisional manner for each one-frame detection. As a result, a first detection signal detected by the optical sensor PD based on the first light and a second detection signal detected by the optical sensor PD based on the second light are output to the detection circuit 48 in a time-division manner.

FIG. 24 is an explanatory diagram for explaining the relation between the driving of the sensor area and the lighting operations of the light sources in the detection device of the present disclosure. In contrast to the comparative example described above where the first and the second light sources 61 and 62 are caused to be on in a time-divisional manner, the first and the second light sources 61 and 62 are caused to be on simultaneously in the present disclosure. As illustrated in FIG. 24, the control circuit 122 simultaneously causes the first and the second light sources 61 and 62 to be on during the period t(1). The first and the second light sources 61 and 62 are also caused to be on simultaneously in the same manner during the periods t(2), t(3) and t(4). The control circuit 122 executes the exposure period Pex and the read period Pdet during each of the periods. As a result, the frame rate can be made higher than that in the case of FIG. 23 where the first and the second light sources 61 and 62 are caused to be on in a time-divisional manner.

Although FIGS. 19 to 23 illustrate the example in which the gate line drive circuit 15 individually selects the gate line GCL, the present disclosure is not limited to this example. The gate line drive circuit 15 may simultaneously select a predetermined number (two or more) of the gate lines GCL, and sequentially supply the gate drive signals Vgcl to the gate lines GCL in units of the predetermined number of the gate lines GCL. The signal line selection circuit 16 may also simultaneously couple a predetermined number (two or more) of the signal lines SGL to the one detection circuit 48. Moreover, the gate line drive circuit 15 may scan some of the gate lines GCL while skipping the others.

As illustrated in FIG. 21, in the row read period VR(1), the selection signals ASW1, . . . , ASW6 are sequentially supplied to the signal line selection circuit 16 during the period in which the gate drive signal Vgcl(1) is at the high-level voltage (power supply voltage VDD). That is, even after the selection signal ASW1 is set to a low-level voltage at time t11, the exposure continues during an exposure period Pex-1 until the gate drive signal Vgcl(1) is set to the low-level voltage at time t13. The signal line SGL(1) corresponding to the selection signal ASW1 is charged with an electric charge corresponding to the exposure period Pex-1 from the optical sensor PD.

In the same manner, each of the signal lines SGL is charged with an electric charge during a corresponding one of exposure periods Pex-1, . . . , Pex-6 corresponding to the selection signals ASW1, . . . , ASW6. For example, the exposure period Pex-6 is a period after the selection signal ASW6 is set to the low-level voltage at time t12 until the gate drive signal Vgcl(1) is set to the low-level voltage at time t13, and the exposure period Pex differs column by column.

Then, in the next row read period VR(2), the detection circuit 48 is supplied with a signal obtained by adding an electric charge stored during the exposure periods Pex-1 (SGL(1)), . . . , Pex-6 (SGL(6)) of the previous row read period VR(1) to the detection signal Vdet of the second row.

As described above, the detection device 1 has the configuration including, for example, a plurality of types of light sources (first light sources 61 and second light sources 62) that emit light having different wave lengths, and thereby, can acquire a fingerprint acquired by detecting the light reflected on the surface of a finger of the subject of examination and the various types of biometric information acquired by detecting the light reflected in or transmitted through the finger, the wrist, or the like of the subject of examination.

Figure 25:
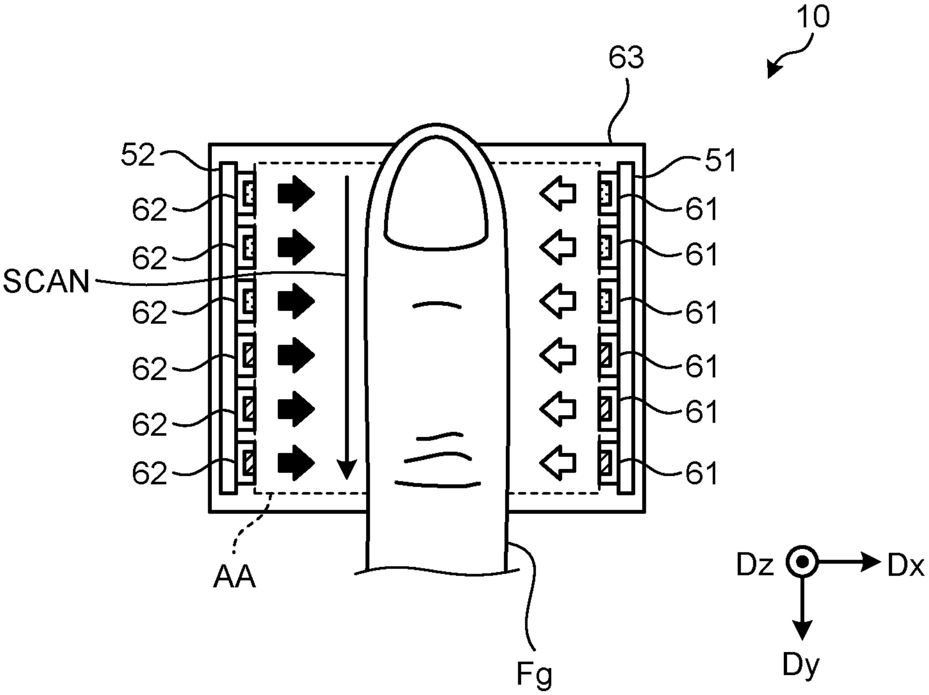
FIG. 25 is a plan view schematically illustrating a relation between the sensor area, first light sources, and second light sources in the detection device according to the embodiment.

As a specific example of the information on the living body acquired by the detection device 1, the following describes an example of acquiring the pulse waves serving as the biometric information for calculating an oxygen saturation level in the blood (hereinafter, called the blood oxygen saturation level (SpO2)). FIG. 25 is a plan view schematically illustrating a relation between the sensor area, the first light sources, and the second light sources in the detection device according to the embodiment.

As illustrated in FIG. 25, the detection device 1 includes a filter 63. The filter 63 is disposed overlapping the detection area AA from one end to the other end of the sensor area 10 in a scan direction SCAN. The filter 63 has a transmission bandwidth for transmitting the first light emitted from the first light sources 61 and the second light emitted from the second light sources 62. In a configuration according to the embodiment, the filter 63 is not required, and the configuration may exclude the filter 63.

In the configuration illustrated in FIG. 25, the scan direction SCAN is the direction in which the gate line drive circuit 15 scans the gate line GCL. That is, one gate line GCL is provided extending in the first direction Dx in the detection area AA, and is coupled to the partial detection areas PAA provided in the detection area AA. One signal line SGL is provided extending in the second direction Dy in the detection area AA, and is coupled to the optical sensors PD in the detection area AA.

The first light source base member 51 and the second light source base member 52 face each other in the first direction Dx with the detection area AA interposed therebetween in the plan view. The first light sources 61 are provided on a surface of the first light source base member 51 facing the second light source base member 52. The second light sources 62 are provided on a surface of the second light source base member 52 facing the first light source base member 51. The first light sources 61 and the second light sources 62 are provided being arranged in the first direction Dx along the periphery of the detection area AA.

The first light sources 61 emit the first light in a direction parallel to the first direction Dx. As a result, the detection area AA is irradiated with the first light. The second light sources 62 emit the second light in a direction parallel to the first direction Dx. As a result, the detection area AA is irradiated with the second light.

Figure 26A:
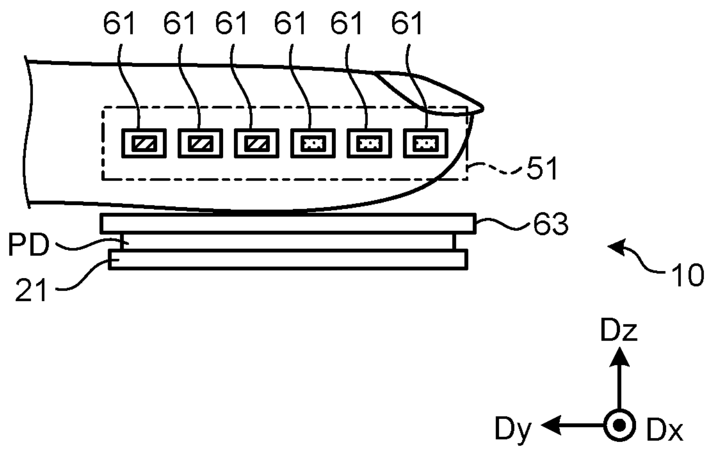
FIG. 26A is a side view of the detection device illustrated in FIG. 25 as viewed in a first direction.
Figure 26B:
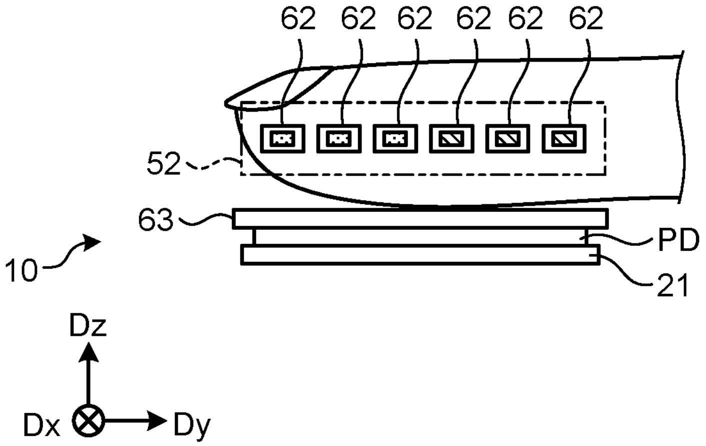
FIG. 26B is a side view of the detection device illustrated in FIG. 25 as viewed in a direction opposite to the first direction.

FIG. 26A is a side view of the detection device illustrated in FIG. 25 as viewed in the first direction Dx. FIG. 26A is a view of the detection device as viewed from the first light source base member 51 side in FIG. 13. FIG. 26B is a side view of the detection device illustrated in FIG. 25 as viewed in a direction opposite to the first direction Dx. FIG. 26B is a view of the detection device as viewed from the second light source base member 52 side in FIG. 13. As illustrated in FIGS. 26A and 26B, the object to be detected such as the finger Fg or the wrist of the subject of examination comes in contact with or in proximity to the top of the sensor area 10 with the filter 63 interposed therebetween. The first and the second light sources 61 and 62 are arranged above the sensor area 10 and the filter 63, and are arranged with the object to be detected such as the finger Fg or the wrist of the subject of examination interposed therebetween in the first direction Dx.

In this example, for example, the green visible light (green light) having a wavelength of 490 nm to 550 nm is employed as the first light emitted from the first light sources 61, and the red visible light (red light) having a wavelength of 640 nm to 770 nm is employed as the second light emitted from the second light sources 62. In the case of acquiring the human blood oxygen saturation level (SpO2), a pulse wave acquired using the first light (green light) and a pulse wave acquired using the second light (red light) are used. The combination of the first and the second light is not limited to green light and red light, but only needs to be a combination that allows the calculation of SpO2. For example, infrared light may be combined with red light. In this case, the combination needs to be such that the ratio of reflectance of oxygenated hemoglobin to that of deoxygenated hemoglobin differs between the first and the second light.

Since the amount of light absorption changes with an amount of oxygen taken up by hemoglobin, the optical sensor PD detects an amount of light obtained by subtracting the amount of light absorbed by the blood (hemoglobin) from that of each of the first light and the second light that have been emitted. Most of the oxygen in the blood is reversibly bound to hemoglobin in red blood cells, and a small portion of the oxygen is dissolved in blood plasma. More specifically, the value of percentage of oxygen with respect to an allowable amount thereof in the blood as a whole is the oxygen saturation level. The blood oxygen saturation level can be calculated from the amount of light obtained by subtracting the amount of light absorbed by the blood (hemoglobin) from that of the light emitted at the two wavelengths of the first light and the second light.

The oxygen saturation level (SpO2) is determined by the ratio of hemoglobin in blood bound to oxygen (oxygenated hemoglobin (O2Hb)) to hemoglobin in blood not bound to oxygen (reduced hemoglobin (HHb). The light absorption characteristics of the red light are represented as HHb>>O2Hb, indicating that HHb has significantly larger absorbance, while, for example, the light absorption characteristics of the infrared light are represented as HHb≈O2Hb, indicating that O2Hb has slightly larger absorbance.

The first light emitted from the first light sources 61 travels in the direction parallel to the first direction Dx and enters the finger Fg or the wrist of the subject of examination. The first light emitted from the first light sources 61 penetrates into the living body, and is reflected in the finger Fg or the wrist of the subject of examination. The reflected light reflected in the finger Fg or the wrist of the subject of examination travels in the third direction Dz, and enters the detection area AA of the sensor area 10 through the filter 63.

The second light emitted from the second light sources 62 travels in the direction parallel to the first direction Dx, and enters the finger Fg or the wrist of the subject of examination. The second light emitted from the second light sources 62 penetrates into the living body and is reflected in the finger Fg or the wrist of the subject of examination. The reflected light reflected in the finger Fg or the wrist of the subject of examination travels in the third direction Dz and enters the detection area AA of the sensor area 10 through the filter 63.

The arrangement of the first and the second light sources 61 and 62 is not limited to the example illustrated in FIGS. 25, 26A, and 26B. For example, in an aspect of the present disclosure, the first and the second light may be emitted from above the object to be detected such as the finger Fg or the wrist of the subject of examination illustrated in FIG. 26A, specifically, in the third direction Dz. Alternatively, the first and the second light sources 61 and 62 may be, for example, what are called direct-type light sources provided directly below the detection area AA.

What is claimed is:

1. A detection device comprising:

a first optical sensor configured to detect light;

a second optical sensor provided adjacent to the first optical sensor and configured to detect lights a first light source configured to emit light having a predetermined wavelength;

a second light source configured to emit light having a wavelength different from that of the light emitted by the first light source;

a controller configured to cause the first light source and the second light source to simultaneously emit the light; and a signal processor configured to perform processing to obtain a blood oxygen saturation level based on a value detected by the first optical sensor and a value detected by the second optical sensor, wherein the first light source, the first optical sensor, the second optical sensor, and the second light source are sequentially arranged, during the first light source being on, and the second light source being off:

the first light sensor is used; and the second sensor is not used, during the second light source being on, and the first light source being off:

the first light sensor is used; and the second light sensor is not used, during the first light source and the second light source being on, the light sensor and the second light sensor are used, and the first optical sensor and the second optical sensor, and the third optical sensor are configured to detect light that has been reflected in a living body or transmitted through the living body.

2. The detection device according to claim 1, wherein the first optical sensor is provided at a location interposed between the second optical sensor and the first light source, and the second optical sensor is provided at a location interposed between the first optical sensor and the second light source.

3. The detection device according to claim 1, wherein the second optical sensor is provided at a location interposed between the first optical sensor and the first light source, and the second optical sensor is provided at a location interposed between the first optical sensor and the second light source.

4. The detection device according to claim 1, wherein, when:

AC(Pix1) denotes an alternating-current component of the value detected by the first optical sensor;

DC(Pix1) denotes a direct-current component of the value detected by the first optical sensor;

AC(Pix2) denotes an alternating-current component of the value detected by the second optical sensor; and DC(Pix2) denotes a direct-current component of the value detected by the second optical sensor, the signal processor is configured to calculate a blood oxygen saturation level SpO2 using the following expression:

$$\mathrm{SpO2} = b' - a' \cdot R'$$

where a' and b' are given coefficients determined in advance, and $$R' = \{\mathrm{AC}(Pix1)/\mathrm{DC}(Pix1)\}/\{\mathrm{AC}(Pix2)/\mathrm{DC}(Pix2)\}.$$

5. A detection device comprising:

a first optical sensor configured to detect light;

a second optical sensor provided adjacent to the first optical sensor and configured to detect light;

a first light source configured to emit light having a predetermined wavelength;

a second light source configured to emit light having a wavelength different from that of the light emitted by the first light source;

a controller configured to cause the first light source and the second light source to simultaneously emit the light;

a signal processor configured to perform processing to obtain a blood oxygen saturation level based on a value detected by the first optical sensor and a value detected by the second optical sensor;

a third optical sensor provided adjacent to the second optical sensor and configured to detect light; and a fourth optical sensor provided adjacent to the third optical sensor and configured to detect light, wherein the first optical sensor, the second optical sensor, the third optical sensor, and the fourth optical sensor are configured to detect light that has been reflected in a living body or transmitted through the living body, and the signal processor is configured to:

calculate a first blood oxygen saturation level SpO2 based on the value detected by the first optical sensor and a value detected by the third optical sensor, calculate a second blood oxygen saturation level SpO2 based on the value detected by the first optical sensor and a value detected by the fourth optical sensor, calculate a third blood oxygen saturation level SpO2 based on the value detected by the second optical sensor and the value detected by the third optical sensor, and calculate a fourth blood oxygen saturation level SpO2 based on the value detected by the second optical sensor and the value detected by the fourth optical sensor; and further calculate an average value of the first blood oxygen saturation level SpO2, the second blood oxygen saturation level SpO2, the third blood oxygen saturation level SpO2, and the fourth blood oxygen saturation level SpO2.

6. The detection device according to claim 5, wherein the signal processor is configured to, when four optical sensors are used, calculate four blood oxygen saturation levels $\mathrm{SpO2}_1$, $\mathrm{SpO2}_2$, $\mathrm{SpO2}_3$, and $\mathrm{SPO2}_4$ using the following expressions:

$$\mathrm{SpO2}_1 = b_1 - a_1 \cdot R_1,$$

$$\text{where } R_1 = \{\mathrm{AC}(Pix1)/\mathrm{DC}(Pix1)\}/\{\mathrm{AC}(Pix3)/\mathrm{DC}\{Pix3\}\};$$

$$\mathrm{SpO2}_2 = b_2 - a_2 \cdot R_2,$$

$$\text{where } R_2 = \{\mathrm{AC}(Pix1)/\mathrm{DC}(Pix1)\}/\{\mathrm{AC}(Pix4)/\mathrm{DC}\{Pix4\}\};$$

$$\mathrm{SpO2}_3 = b_3 - a_3 \cdot R_3,$$

$$\text{where } R_3 = \{\mathrm{AC}(Pix2)/\mathrm{DC}(Pix2)\}/\{\mathrm{AC}(Pix3)/\mathrm{DC}\{Pix3\}\}; \text{ and}$$

$$\mathrm{SpO2}_4 = b_4 - a_4 \cdot R_4,$$

$$\text{where } R_4 = \{\mathrm{AC}(Pix2)/\mathrm{DC}(Pix2)\}/\{\mathrm{AC}(Pix4)/\mathrm{DC}\{Pix4\}\}, \text{ and}$$

further calculate an average value SpO2 of the four blood oxygen saturation levels using the following expression:

$$\mathrm{SpO2} = (\mathrm{SpO2}_1 + \mathrm{SpO2}_2 + \mathrm{SpO2}_3 + \mathrm{SpO2}_4)/4.$$

7. The detection device according to claim 1, wherein the first optical sensor and the second optical sensor are organic photodiodes.

8. The detection device according to claim 5, wherein the first optical sensor is provided at a location interposed between the second optical sensor and the first light source, and the second optical sensor is provided at a location interposed between the first optical sensor and the second light source.

9. The detection device according to claim 5, wherein the second optical sensor is provided at a location interposed between the first optical sensor and the first light source, and the second optical sensor is provided at a location interposed between the first optical sensor and the second light source.

10. The detection device according to claim 5, wherein, when:

AC(Pix1) denotes an alternating-current component of the value detected by the first optical sensor;

DC(Pix1) denotes a direct-current component of the value detected by the first optical sensor;

AC(Pix2) denotes an alternating-current component of the value detected by the second optical sensor; and DC(Pix2) denotes a direct-current component of the value detected by the second optical sensor, the signal processor is configured to calculate the blood oxygen saturation level SpO2 using the following expression:

$$\mathrm{SpO2} = b' = a' \cdot R'$$

where a' and b' are given coefficients determined in advance, and $$R' = \{\mathrm{AC}(Pix1)/\mathrm{DC}(Pix1)\}/\{\mathrm{AC}(Pix2)/\mathrm{DC}(Pix2)\}.$$

11. The detection device according to claim 1, further comprising a third optical sensor provided adjacent to the second optical sensor and configured to detect light, wherein the third optical sensor is configured to detect light that has been reflected in the living body or transmitted through the living body, and the signal processor is configured to:

calculate blood oxygen saturation levels SpO2 using respective values detected by any two of the first optical sensor, the second optical sensor, and the third optical sensor; and calculate an average value of the calculated blood oxygen saturation levels SpO2.

12. The detection device according to claim 11, wherein the signal processor is configured to, when four optical sensors are used, calculate four blood oxygen saturation levels $\mathrm{SpO2}_1$, $\mathrm{SpO2}_2$, $\mathrm{SpO2}_3$, and $\mathrm{SPO2}_4$ using the following expressions:

$$\mathrm{SpO2}_1 = b_1 - a_1 \cdot R_1,$$

$$\text{where } R_1 = \{\mathrm{AC}(Pix1)/\mathrm{DC}(Pix1)\}/\{\mathrm{AC}(Pix3)/\mathrm{DC}\{Pix3)\};$$

$$\mathrm{SpO2}_2 = b_2 - a_2 \cdot R_2,$$

$$\text{where } R_2 = \{\mathrm{AC}(Pix1)/\mathrm{DC}(Pix1)\}/\{\mathrm{AC}(Pix4)/\mathrm{DC}\{Pix4)\};$$

$$\mathrm{SpO2}_3 = b_3 - a_3 \cdot R_3,$$

$$\text{where } R_3 = \{\mathrm{AC}(Pix2)/\mathrm{DC}(Pix2)\}/\{\mathrm{AC}(Pix3)/\mathrm{DC}\{Pix3)\}; \text{ and}$$

$$\mathrm{SpO2}_4 = b_4 - a_4 \cdot R_4,$$

$$\text{where } R_4 = \{\mathrm{AC}(Pix2)/\mathrm{DC}(Pix2)\}/\{\mathrm{AC}(Pix4)/\mathrm{DC}\{Pix4)\}, \text{ and}$$

further calculate an average value SpO2 of the four blood oxygen saturation levels using the following expression:

$$\mathrm{SpO2} = (\mathrm{SpO2}_1 + \mathrm{SpO2}_2 + \mathrm{SpO2}_3 + \mathrm{SpO2}_4)/4.$$

* * * * *